(12) United States Patent
Long et al.

(10) Patent No.: US 8,575,345 B2
(45) Date of Patent: Nov. 5, 2013

(54) MOLECULAR COBALT PENTAPYRIDINE CATALYSTS FOR GENERATING HYDROGEN FROM WATER

(75) Inventors: Jeffrey R. Long, Oakland, CA (US); Christopher J. Chang, Berkeley, CA (US); Yujie Sun, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/475,788

(22) Filed: May 18, 2012

(65) Prior Publication Data

US 2012/0296092 A1 Nov. 22, 2012

Related U.S. Application Data

(60) Provisional application No. 61/488,016, filed on May 19, 2011.

(51) Int. Cl.
*C07F 15/00* (2006.01)

(52) U.S. Cl.
USPC .............................................. 546/2

(58) Field of Classification Search
USPC .............................................. 546/2
See application file for complete search history.

(56) References Cited

PUBLICATIONS

Zadrozny et al Inorganic Chemistry 2010, 49, 8886-8896.*

\* cited by examiner

*Primary Examiner* — John Mabry
(74) *Attorney, Agent, or Firm* — Lawrence Berkeley National Laboratory

(57) ABSTRACT

A composition of matter suitable for the generation of hydrogen from water is described, the positively charged cation of the composition including the moiety of the general formula. $[(PY5Me_2)CoL]^{2+}$, where L can be $H_2O$, $OH^-$, a halide, alcohol, ether, amine, and the like. In embodiments of the invention, water, such as tap water or sea water can be subject to low electric potentials, with the result being, among other things, the generation of hydrogen.

1 Claim, 24 Drawing Sheets

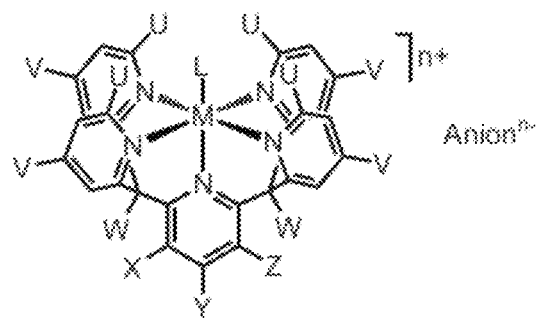

M = Co (or other transition metal)

U, V, W, X, Y, and Z are H, R, a halide, $CF_3$, $SiR_3$, where R can be an alkyl or aryl group L can be $H_2O$, $OH^-$, halide, alcohol, ether, thioether, amine, phosphine, nitrile, thiol, alkoxide, cyanide, isocyanide, azide, thiocyanate, sulfonate, phosphate n = 0, 1, 2, or 3

Anions can be selected from chloride, phosphate, trifluoromethanesulfonate, hexafluorophosphate

FIG. 6

MOLECULAR COBALT PENTAPYRIDINE CATALYSTS FOR GENERATING HYDROGEN FROM WATER

CROSS REFERENCE TO RELATED APPLICATIONS

This United States Patent Application claims priority to U.S. Provisional Application Ser. No. 61/488,016 filed May 19, 2011, which application is incorporated herein by reference as if fully set forth in their entirety.

This application relates to both U.S. Provisional Patent Application Ser. No. 61/446,400, filed Feb. 24, 2011, entitled Molecular Molybdenum Persulfide and Related Catalysts for Generating Hydrogen from Water, and PCT Patent Application Serial No. PCT/US2010/048405, filed Sep. 10, 2010, entitled Molecular Metal-Oxo Catalysts for Generating Hydrogen from Water, which PCT application claims priority to U.S. Provisional Patent Application 61/249,847, filed Oct. 8, 2009, all of which applications are incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231, and the National Science Foundation under Contract No. CHE-0617063. The government has certain rights in this invention.

BACKGROUND OF THE INVENTION

1. Field of the Invention

This invention relates generally to a new composition of matter and, more specifically, to a new molecular electrocatalyst composed of inexpensive and abundant metals, capable of generating hydrogen from neutral water under ambient conditions at high rates with minimal applied potential, in one embodiment the metal being cobalt.

2. Brief Description of the Related Art

Owing to issues of climate change and accelerating global energy demands, the search for viable carbon-neutral sources of renewable energy is amongst the foremost challenges in science today. One such alternative is hydrogen, which can potentially be used as a clean replacement for fossil fuels in many applications, including transportation in cars, buses, trucks, trains, and airplanes. It can further be used in fuel cells for powering mobile devices such as lap-top computers and cell phones, as well as for meeting power requirements in buildings and industry. Many industries also use hydrogen as a reactant. One example is the Haber-Bosch process that produces ammonia, which currently relies on steam reforming of natural gas or liquefied petroleum for the production of hydrogen. This is expensive, environmentally unsustainable (based on finite resources of fossil fuel and produces carbon dioxide and hydrogen sulfide, two major atmospheric pollutants) and necessitates removal of sulfur which deactivates the catalyst used for ammonia production. Hydrogen is also used as a reducing agent for metal ores, for the production of hydrochloric acid and as a hydrogenating agent for unsaturated fats and oils.

this context, where hydrogen has emerged as an attractive candidate for a clean, sustainable fuel as well as a precursor to many essential compounds, an intense interest in creating artificial systems that utilize earth-abundant catalysts for efficient hydrogen production from water has developed. A major quest of this renewable energy research is the search for efficient catalysts for the production of hydrogen from water, which rely on cheap, earth-abundant elements.

Hydrogenase enzymes possessing earth-abundant iron and/or nickel cofactors have been found to catalytically evolve $H_2$ from neutral aqueous solution at its thermodynamic potential, with turnover frequencies of 100-10,000 mol $H_2$/mol catalyst per second. However, the large size and relative instability of these enzymes under aerobic, ambient conditions has led to the search for well-defined molecular complexes outside the biological milieu that can produce $H_2$ from water. Although many examples of air- and moisture-sensitive synthetic iron-sulfur clusters have provided insight into hydrogenase structure and reactivity, they catalyze proton reduction from acids in organic solvents at fairly negative potentials of −0.9 to −1.8 V vs. SHE (the Standard Hydrogen Electrode). Metal complexes that evolve $H_2$ at more positive potentials still require organic acids, additives, and/or solvents, As such, the creation of earth-abundant molecular systems that produce $H_2$ from water with high catalytic activity and stability remains a significant basic scientific challenge.

In related PCT application PCT/US2010/048405 described was a high oxidation state metal-oxo compound that catalytically generates hydrogen from water at neutral pH. In one embodiment, the organo metal-oxo complex is an organo molybdenum-oxo complex, which was successfully used to generate hydrogen for at least 3 days, with a turnover frequency (TOF) of at least 1.47 mol $H_2$/mol catalyst per hour (i.e., 408 mol $H_2$/mol catalyst per second) and a turnover number (TON) of 105 million mol $H_2$/mol catalyst. Moreover, this same molecular system was used to evolve $H_2$ from seawater, the earth's most abundant source of protons.

In more recently filed Provisional Application 61/446,400, reported was another new composition of matter having the ability to catalyze the generation of hydrogen from water, wherein the cation of the composition was represented by the general formula $[(PY5W_2)MS_2]^{x+}$, where in one embodiment the metal was Mo. This composition was found to have the ability to catalyze the generation of hydrogen from water with turnover frequencies (TOFs) reaching approximately 500 moles $H_2$ per mole catalyst per second and turnover numbers (TONs) reaching (in one experiment run for 20 hours) over 19,000,000 moles $H_2$ per mole of catalyst. Also described therein was a species of the persulfido $[(PY5W_2)MoS_2]^{2+}$ complex where W in one embodiment was methyl, the $MoS_2$ containing salt used as a catalyst to generate hydrogen from water at low pH, especially at pHs significantly lower than 7.

Notwithstanding these results, there still remains a need for even cheaper, more efficient catalysts for the generation of hydrogen from water.

BRIEF SUMMARY OF THE INVENTION

According to the invention, a set of robust molecular cobalt catalysts for the generation of hydrogen from water are described. This cobalt complex, supported by a parent pentadentate polypyridyl ligand PY5Me$_2$, features high stability and activity and 100% Faradaic efficiency for the electrocatalytic production of hydrogen from neutral water, with a turnover number reaching $5.5 \times 10^4$ moles of $H_2$ per mole of catalyst with no loss in activity over 60 h. Further experiments demonstrate that the overpotentials for $H_2$ evolution can be tuned by systematic substitutions on the ancillary PY5Me$_2$ scaffold, presaging opportunities to further optimize this first-generation platform by molecular design.

The rates of hydrogen production using these organo metal catalysts are at least one to two orders of magnitude higher than other known molecular cobalt electro catalysts in neutral aqueous media. The cost of cobalt is about 200 times lower than the cost of platinum, the current catalyst used for hydrogen production.

BRIEF DESCRIPTION OF THE DRAWINGS

The foregoing aspects and others will be readily appreciated by the skilled artisan from the following description of illustrative embodiments when read in conjunction with the accompanying drawings.

FIG. 6 is a structural depiction of the Co—PY5Me$_2$ composition of the invention.

DETAILED DESCRIPTION

Figure 1:
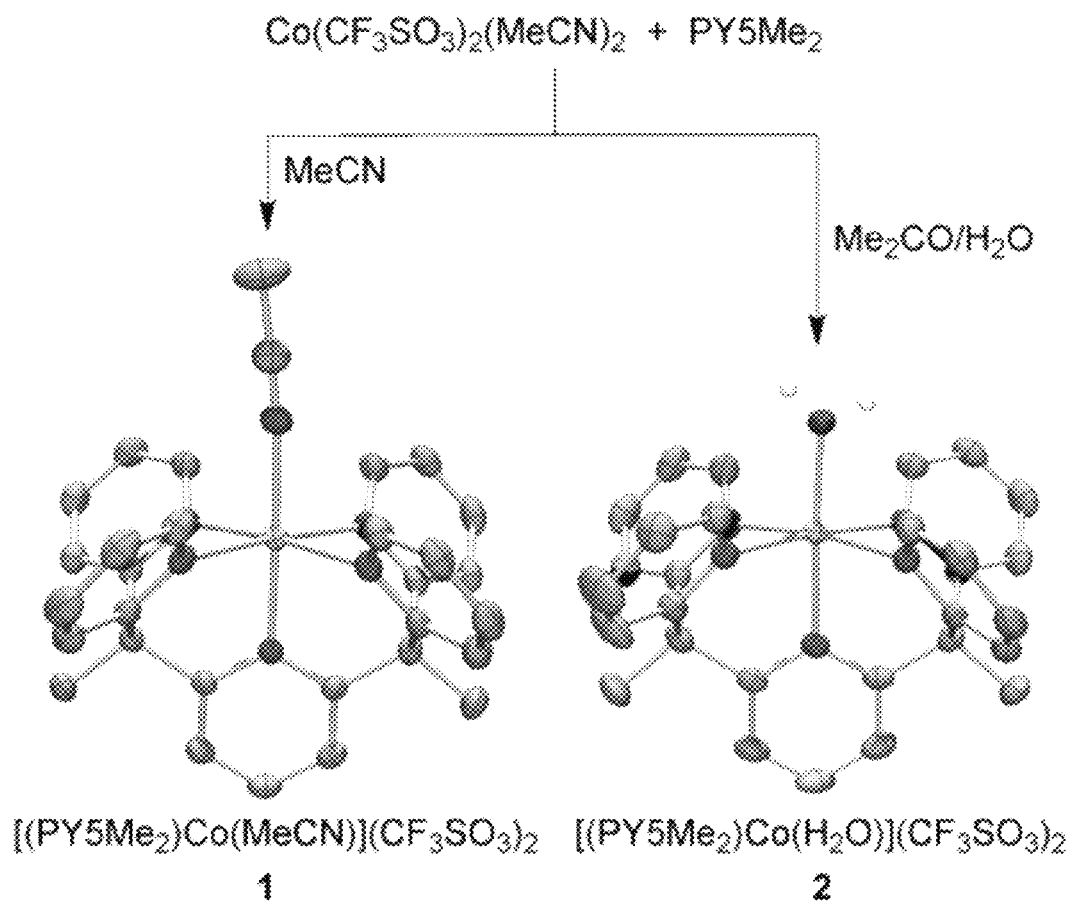
FIG. 1 illustrates the synthesis of compounds 1 and 2, and crystal structures of the complexes $[(PY5Me_2)Co(MeCN)]^{2+}$ and $[(PY5Me_2)Co(H_2O)]^{2+}$ with thermal ellipsoids drawn at the 50% probability level. Selected interatomic distances (Å) and angles (deg): 1: $Co-N_{Py}$ 2.095(3)-2.142(3), $Co-N_{MeCN}$ 2.123(3), $N_{Py}-Co-N_{Py}$ 80.4(1)-99.6(1), $N_{Py}-Co-N_{MeCN}$ 91.8(1)-94.3(1); 2: Co—N 2.103(2)-2.150(1), Co—O 2.055(2), N—Co—N 80.83(8)-101.59(8), N—Co—O 91.12(7)-96.30(8).

The preferred embodiments are illustrated in the context of the use of a cobalt catalyst for the generation of hydrogen. The skilled artisan will readily appreciate, however, that the materials and methods disclosed herein will have application to a number of variants of this composition.

It has been discovered that a certain class of molecules can be particularly useful as catalysts for the generation of hydrogen gas from water. More particularly, these molecules are salts wherein the positive moiety comprises a PY5 cobalt metal ion represented by the structural formula illustrated in FIG. 6.

Growing global energy demand and concerns over climate change mediated by greenhouse gases released upon burning fossil fuels are driving the development of alternative and sustainable energy sources. Hydrogen, when derived from carbon-neutral processes, is an attractive clean fuel candidate for renewable energy storage and transport. In this regard, well-defined molecular catalysts, particularly those that utilize cheap and earth-abundant metals, provide an appealing approach toward $H_2$ production owing to the potential to understand and tune performance through chemical design. Nature has evolved iron- and/or nickel-dependent hydrogenase enzymes for producing $H_2$ from aqueous media with high efficiency and activity, but the large size and relative instability of these molecules under aerobic conditions present challenges for their use in artificial devices. Whereas many beautiful examples of $H_2$-evolution catalysts that mimic the inner workings of such enzymes have been developed, most requirk. the use of organic acids and fairly negative potentials. In addition, abiotic earth-abundant metal complexes featuring cobalt, nickel, and molybdenum have been shown to generate $H_2$ at less extreme potentials, but many of these catalysts still utilize organic solvents, acids, and/or additives that result in organic byproducts. Thus, creating molecules for $H_2$ generation from water that are based upon earth-abundant elements, require no organic additives, and maintain high efficiency and activity in aqueous media remains a significant challenge. Here, we demonstrate that a pentapyridine ligand with adjustable donor properties can provide new molecular cobalt complexes for robust, efficient, and active electrocatalytic $H_2$ generation from neutral pH water without organic additives.

We have initiated a program aimed at developing molecular catalysts for reactions relevant to sustainable energy cycles, with specific efforts focusing on the use of polypyridyl ancillary ligands to support reactive earth-abundant metal complexes that are stable and maintain their activity in benign aqueous media. Recently, a cobalt complex supported by the tetradentan ligand 2-bis(2-pyridyl)(methoxy)methyl-6-pyridylpyridine (PY4) was catalyze the reduction of protons to $H_2$ in 50% aqueous media, whereas a molybdenum-oxo complex ligated by the pentadentate platform 2,6-bis(1,1-bis(2-pyridyl)ethyl)pyridine ($PY5Me_2$) was demonstrated to facilitate the generation of $H_2$ from neutral pH water or even sea water. Encouraged by these findings and related work on biomimetic PY5 oxidation chemistry, we reasoned that exploring first-row transition metal complexes supported by $PY5Me_2$ and related platforms could afford systems for reductive catalysis with aqueous compatibility.

FIG. 1 illustrates the synthesis of compounds 1 and 2, and crystal structures of the complexes $[(PY5Me_2)Co(MeCN)]^{2+}$ and $[(PYM5Me_2)Co(H_2O)]^{2+}$ with thermal ellipsoids drawn at the 50% probability level, Selected interatomic distances (Å) and angles (deg): 1: Co—$N_{Py}$ 2.095(3)-2.142(3), Co—$N_{MeCN}$ 2.123(3), $N_{Py}$—Co—$N_{Py}$ 80.4(1)-99.6(1), $N_{Py}$—Co—$N_{MeCN}$ 91.8(1)-94.3(1); 2: Co—N 2.103(2)-2.150(1), Co—O 2.055(2), N—Co—N 80.83(8)-101.59(8), N—Co—O 91.12(7)-96.30(8).

Figure 7:
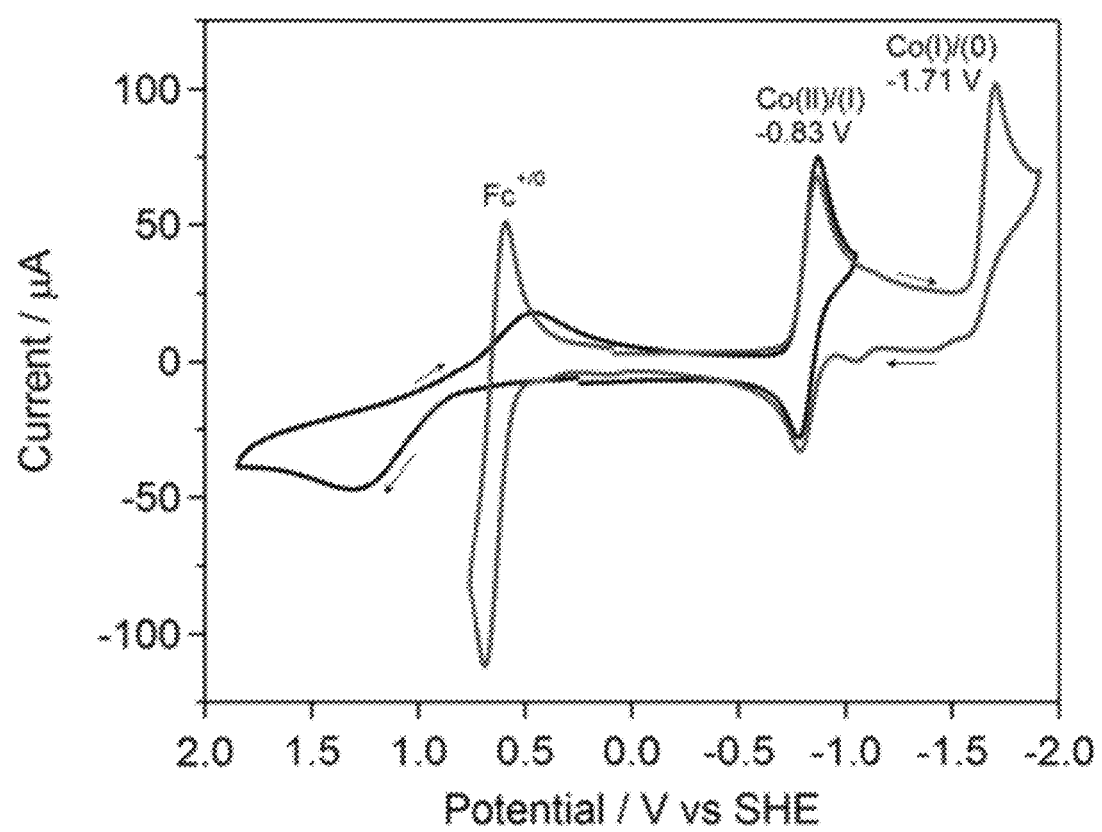
FIG. 7 illustrates cyclic voltammograms of 1 in CH$_3$CN with (red) and without (black) the internal reference ferrocene ($E_{Fc}^{+/0}$=0.64 V vs. SHE; scan rate: 100 mV/s).
Figure 8:
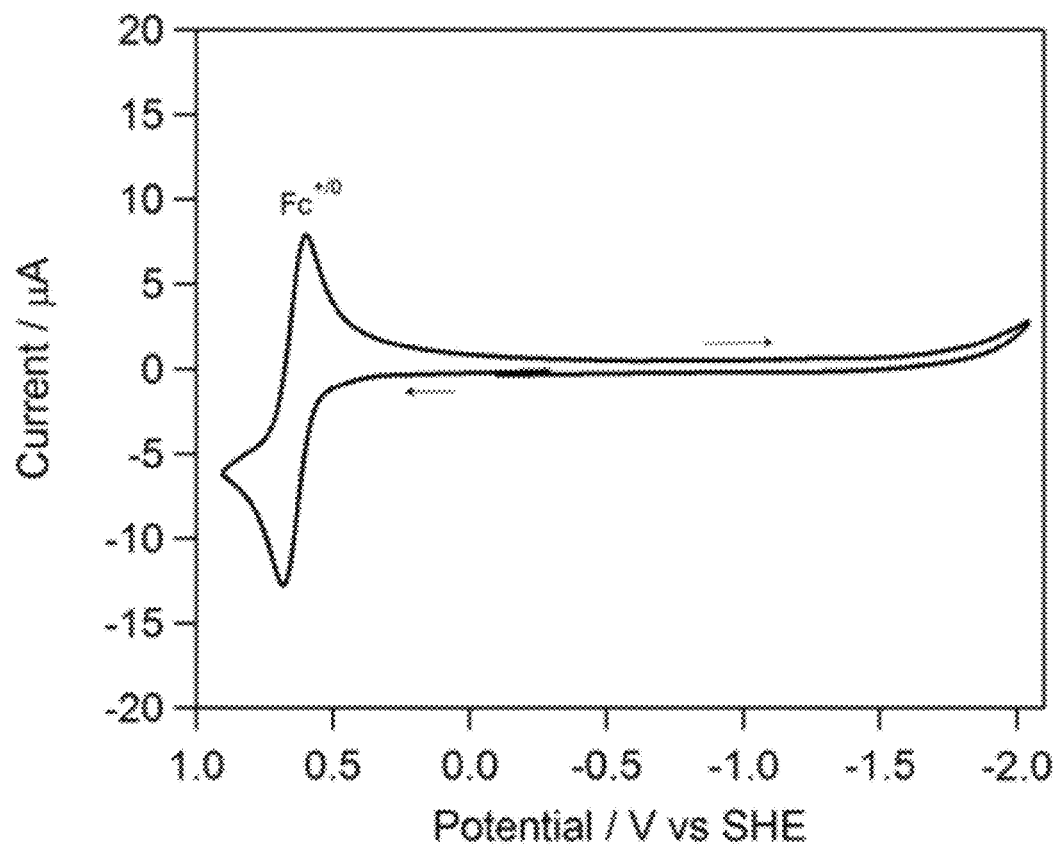
FIG. 8 illustrates cyclic voltammogram of PY5Me$_2$ in CH$_3$CN and the ferrocene peak ($E_{Fc}^{+/0}$=064 V vs. SHE) included as the reference (scan rate: 100 mV/s)
Figure 9:
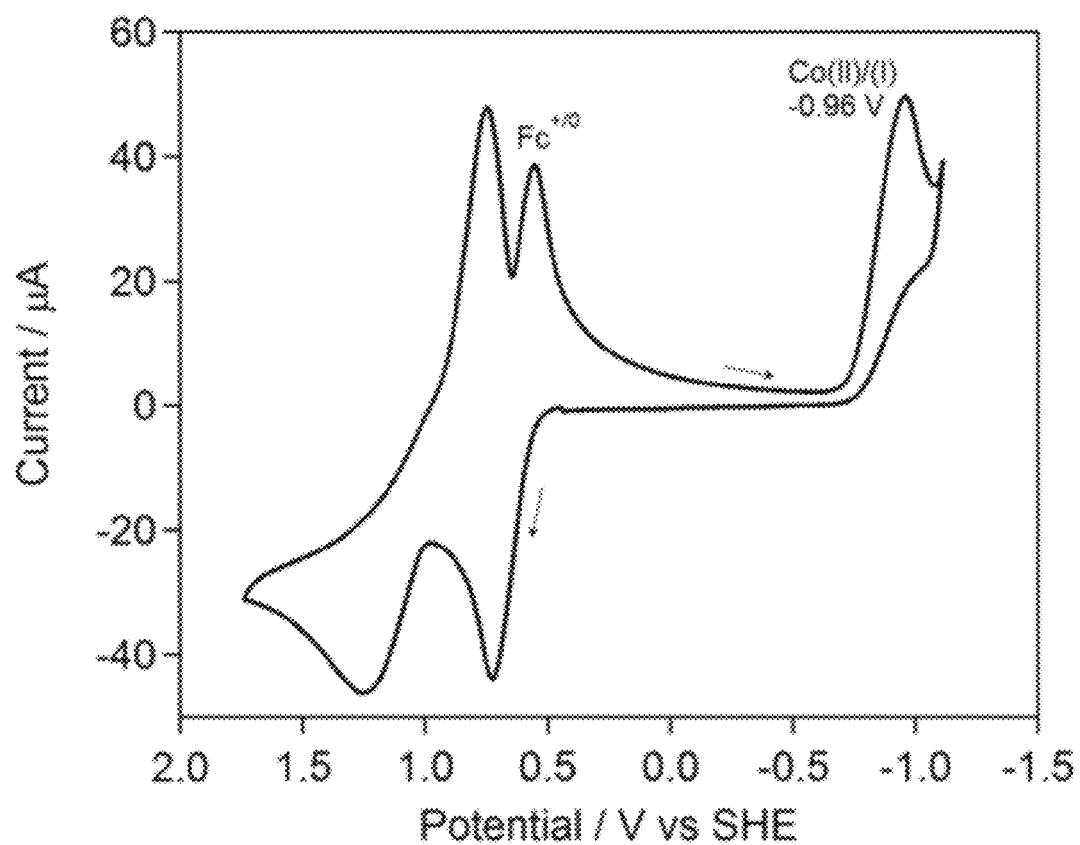
FIG. 9 illustrates cyclic voltammogram of 1 in CH$_2$Cl$_2$ and the ferrocene peak ($E_{Fc}^{+/0}$=0.64 V vs. SHE) included as the reference (scan rate: 100 mV/s).

Metallation of $PY5Me_2$ with $Co(CF_3SO_3)_2(MeCN)_2$ in acetonitrile proceeds smoothly at room temperature to afford $[(PY5Me_2)Co(MeCN)](CF_3SO_3)_2$ (1) (FIG. 1). Consistent with the structure of the $PF_6^-$ analog, the Co(II) center in $[(PY5Me_2)Co(MeCN)]^{2+}$ resides in a slightly distorted octahedral geometry with acetonitrile bound at the apical site. The cyclic voltammogram of 1 in acetonitrile solution features a reversible redox couple at $E_{1/2}$=−0.83 V vs. SHE assigned to a metal-based Co(II)/Co(I) reduction, with a second irreversible reduction peak arising at −1.72 V vs. SHE (FIG. 7). A quasi-reversible oxidative wave at +0.88 V vs. SHE can further be assigned to a Co(II)/Co(III) oxidation event. The free $PY5Me_2$ ligand is electrochemically silent in this potential range (FIG. 8). When the cyclic voltammogram of 1 is measured in dichloromethane, the Co(II)/Co(I) reduction appears as an electrochemically irreversible peak at −0.96 V vs. SHE (FIG. 9).

Figure 2:
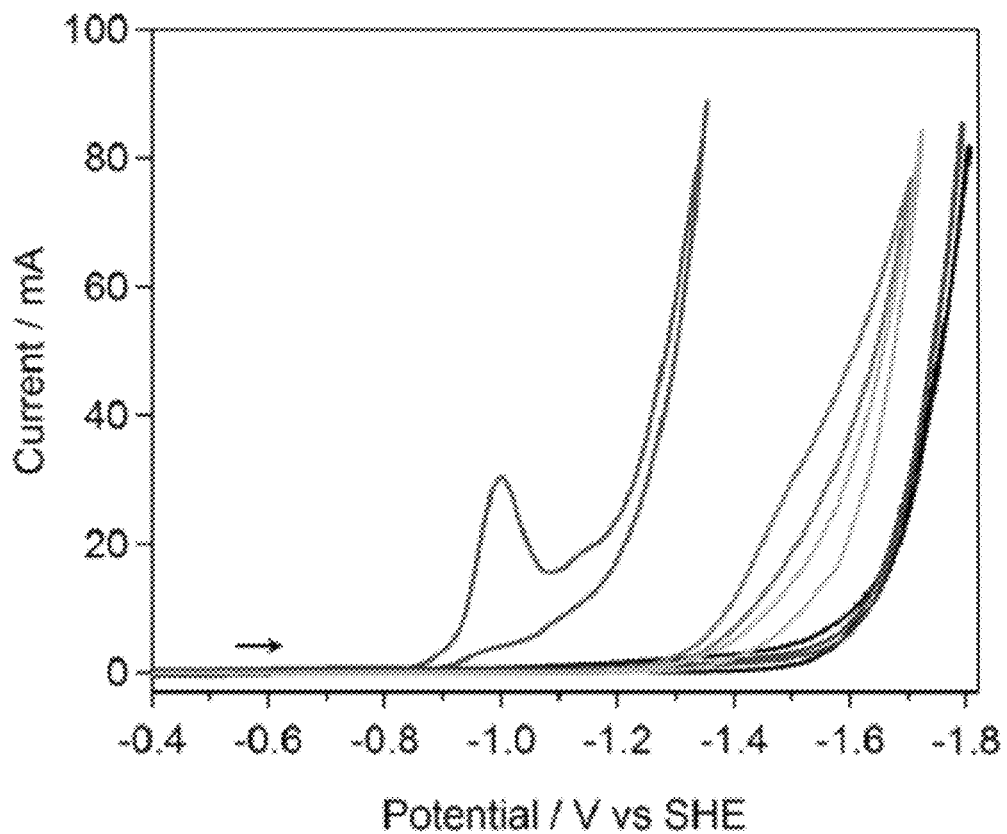
FIG. 2 is a plot of cyclic voltammograms of 71 µM Co(II)-PY5Me$_2$ complex 2 (red), 67 µM Zn(II)-PY5Me$_2$ complex 3 (orange), 16 µM PY5Me$_2$ (green), 93 µM CoCl$_2$ (blue), or blank control (black) measured in aqueous solution buffered to neutral pH (1.0 M phosphate, pH 7). Only the Co(II)-PY5Me$_2$ complex 2 markedly lowers the overpotential for generating H$_2$ from water compared to the bare electrode.

FIG. 2 illustrates Cyclic voltammograms of 71 μM Co(II)-$PY5Me_2$ complex 2 (red), 67 μM Zn(II)-$PY5Me_2$ complex 3 (orange), 16 μM $PY5Me_2$ (green), 93 μM $CoCl_2$ (blue), or blank control (black) measured in aqueous solution buffered to neutral pH (1.0 M phosphate, pH 7). Only the Co(II)-$PY5Me_2$ complex 2 markedly towers the overpotential for generating $H_2$ from water compared to the bare electrode.

Figure 10:
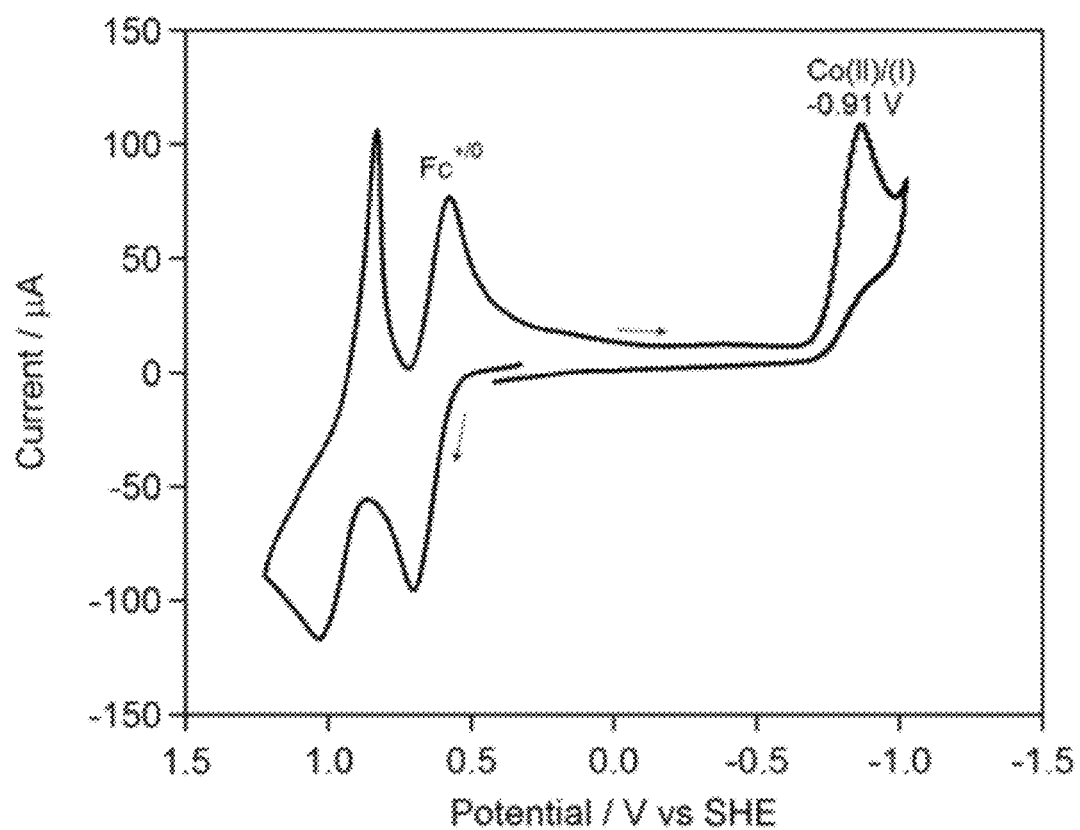
FIG. 10 illustrates cyclic voltammogram of 2 in CH$_2$Cl$_2$ and the ferrocene peak ($E_{Fc}^{+/0}$=0.64 V vs. SHE) included as the reference (scan rate: 100 mV/s).
Figure 11:
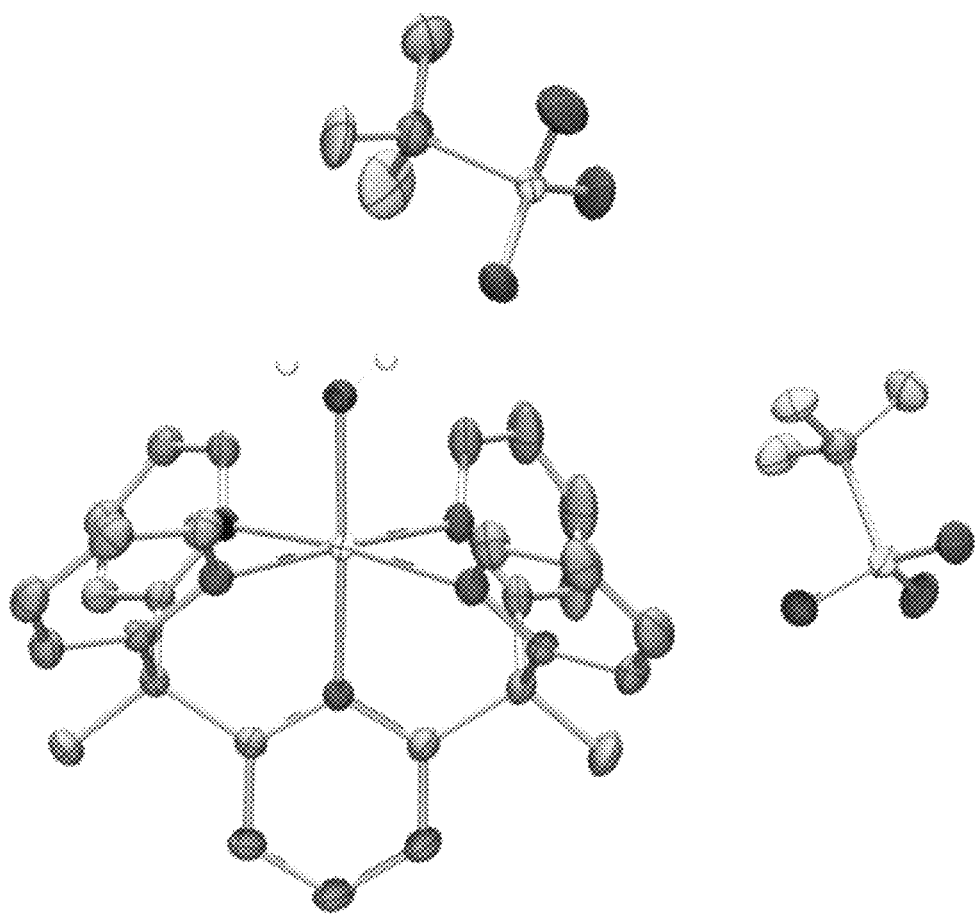
FIG. 11 illustrates X-ray crystal structure of the complex $[(PY5Me_2)Zn(H_2O)](CF_3SO_3)_2$ (3) with thermal ellipsoids drawn at the 75% probability level.

To avoid any possible influence from acetonitrile when investigating the electrochemistry in water, the metallation of $PY5Me_2$ was carried also out with $Co(CF_3SO_3)_2(MeCN)_2$ in a 9:1 acetone/water mixture, resulting in the isolation of $[(PY5Me_2)Co(H_2O)](CF_3SO_3)_2$ (2) (FIG. 1). The crystal structure of 2 confirms the expected octahedral geometry for $[(PYM5Me_2)Co(H_2O)]^{2+}$ with a coordinated apical water ligand, The voltammogram of 2 in dichloromethane is qualitatively similar to that observed for with the irreversible reductive peak shifted by +0.05 V to −0.91 V vs. SHE (FIG. 10). A quasi-reversible oxidative wave is also observed at +0.93 V vs. SHE with a shape peak suggestive of an electrochemical stripping process. Here again, the observed features can be assigned to Co(II)/Co(I) and Co(II)/Co(III) redox changes, respectively. To check that these processes are indeed associated with metal-centered instead of ligand-based redox changes, the compound $[(PY5Me_2)Zn(H_2O)](CF_3SO_3)_2$. (3) was synthesized for comparison (see Supporting Information), The crystal structure of 3 is shown in FIG. 11. The absence of any redox processes for the analogous octahedral complex of the redox-inactive Zn(II) ion within the potential window of dichloromethane FIG. 12) confirms that the ligand alone is not responsible for the redox chemistry observed for 2.

Figure 13:
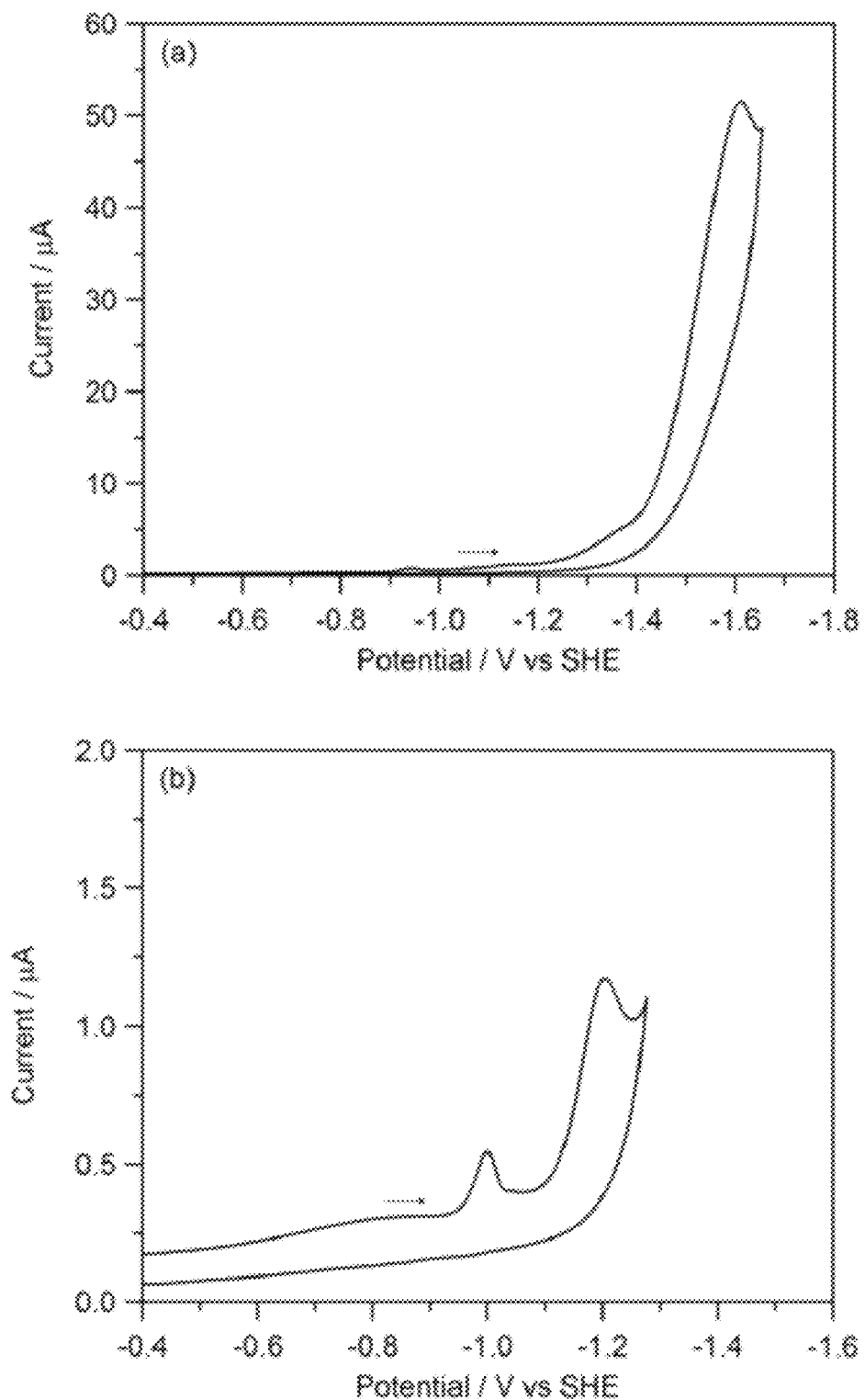
FIG. 13 illustrates cyclic voltammogram of 3.7 µM 2 scanned to −1.66 V (a) and −1.28 V (b) vs. SHE in 0.05 M phosphate buffer at pH 7 (scan rate: 100 mV/s).
Figure 14:
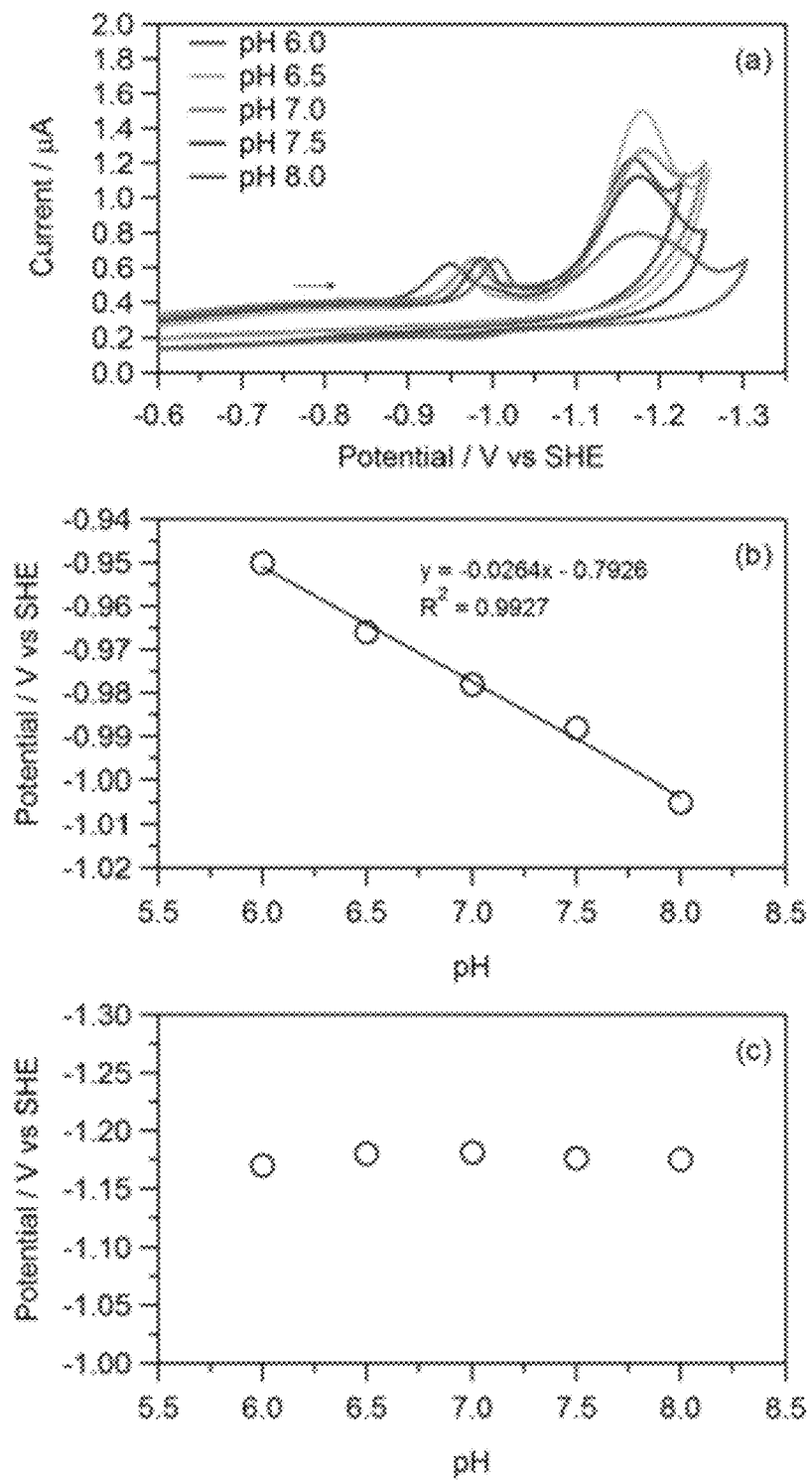
FIG. 14 illustrates cyclic voltammogram (a), the first (b) and second (c) reduction potentials of 3.7 µM 2 in 0.05 M phosphate buffer as a function of pH (scan rate: 100 mV/s).
Figure 15:
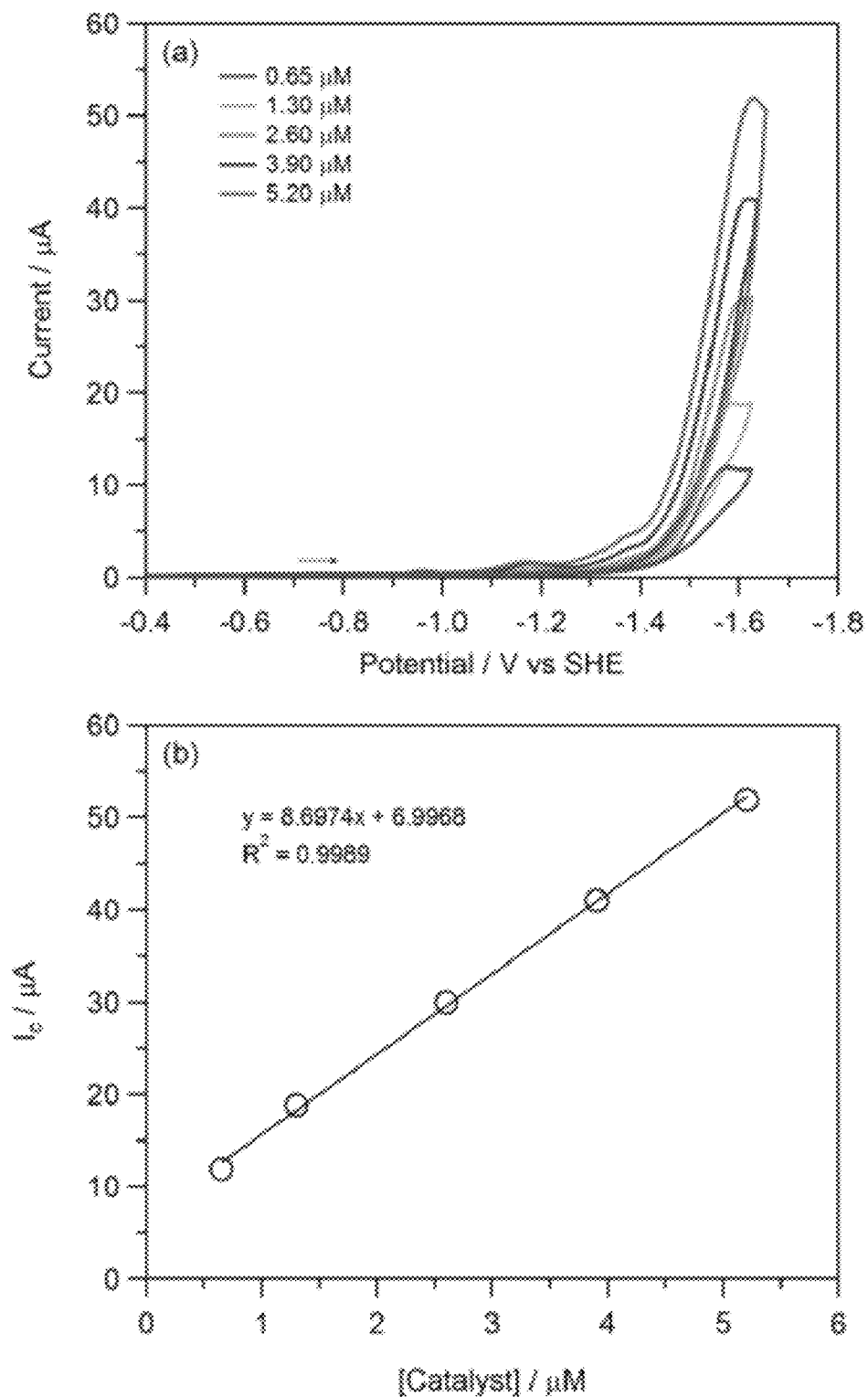
FIG. 15 illustrates (a) cyclic voltammogram and (b) catalytic current maximum ($I_c$) of 2 in 0.05 M phosphate buffer (pH 7) as a function of the catalyst concentration (scan rate: 100 mV/s).
Figure 16:
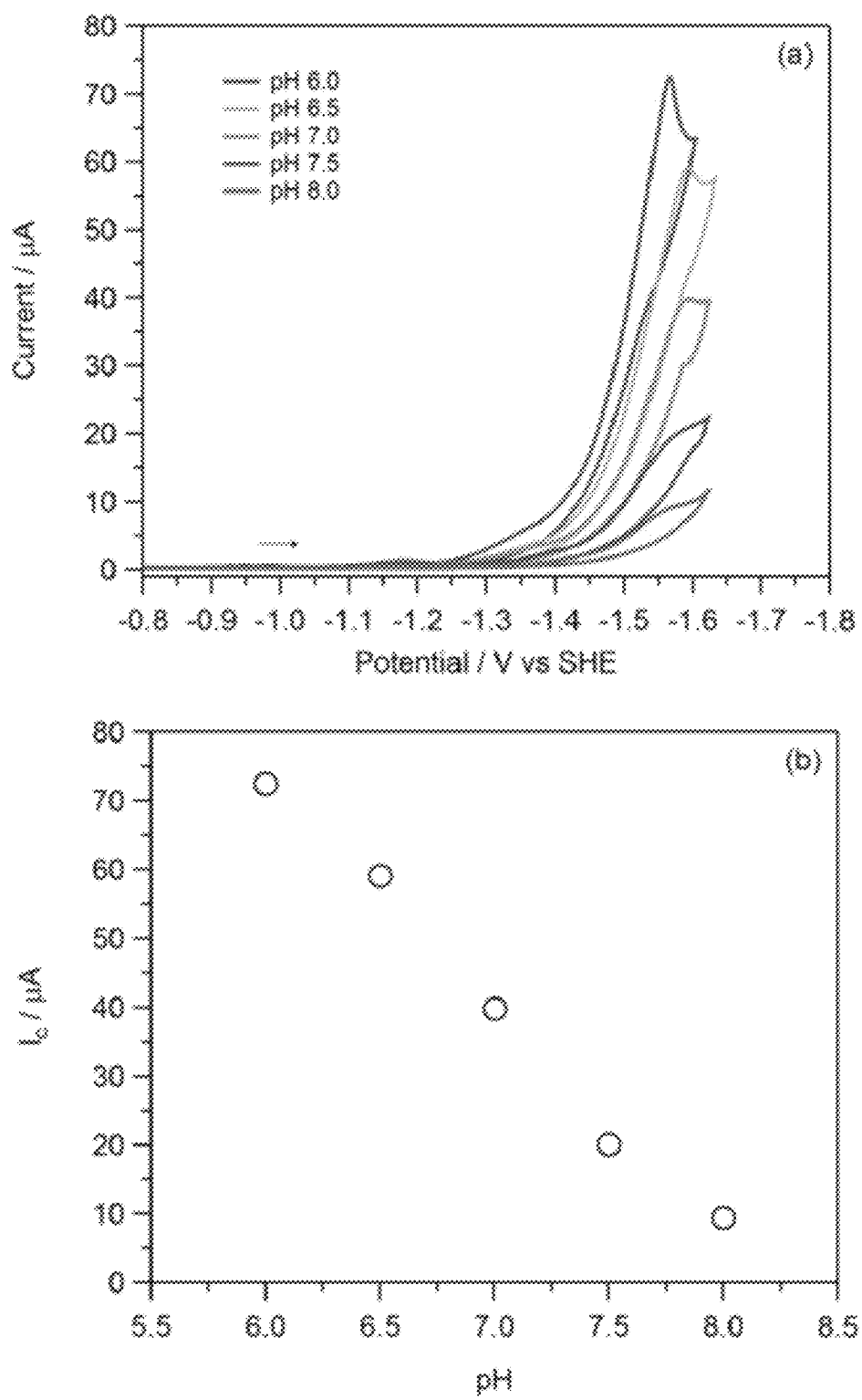
FIG. 16 illustrates (a) cyclic voltammogram and (b) catalytic current maximum ($I_c$) of 3.7 µM in 0.05 M phosphate buffer as a function of pH (scan rate: 100 mV/s).
Figure 17:
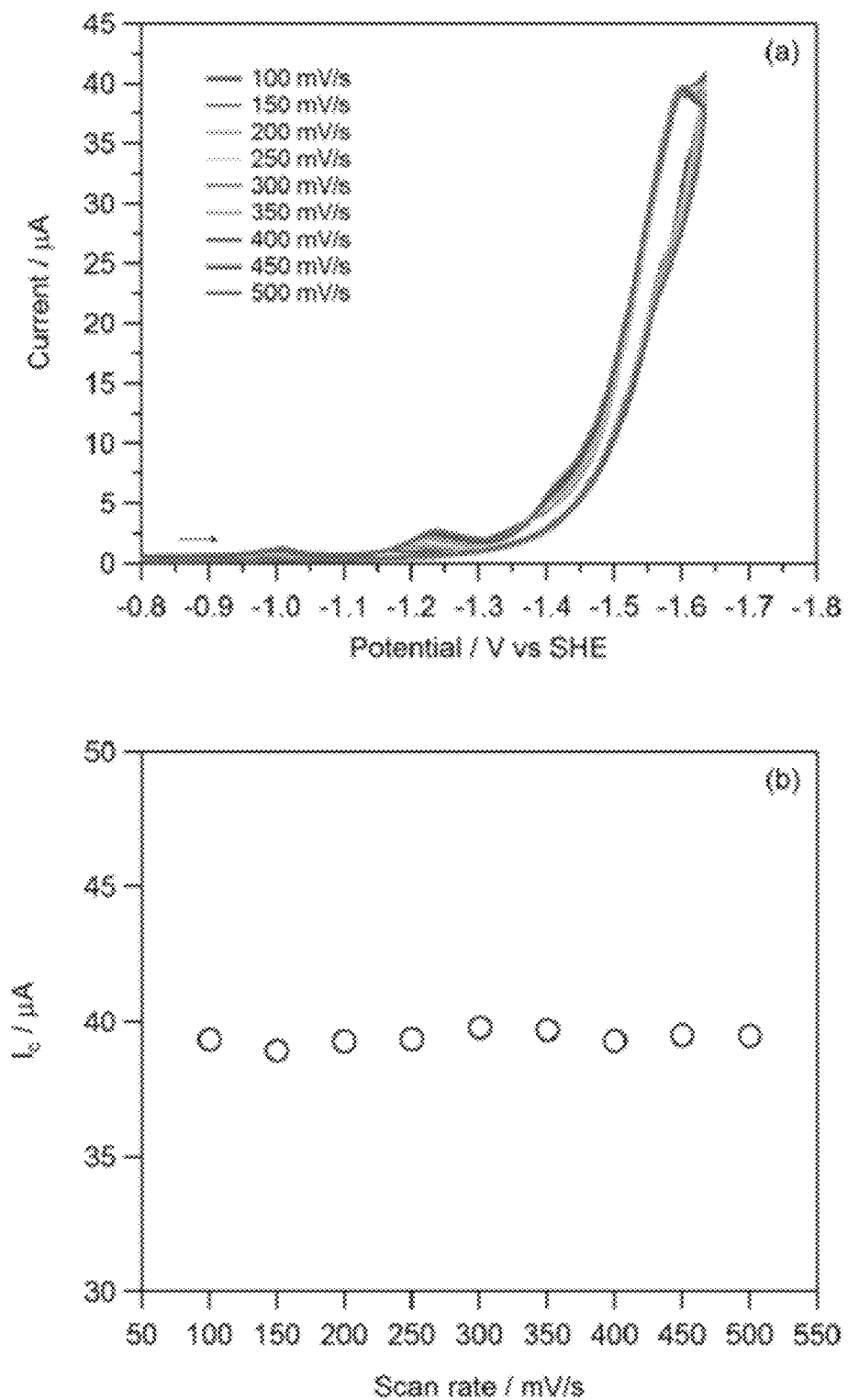
FIG. 17 illustrates (a) cyclic voltammogram and (b) catalytic current maximum ($I_c$) of 3.1 µM 2 in 0.05 M phosphate buffer (pH 7) as a function of scan rate.
Figure 18:
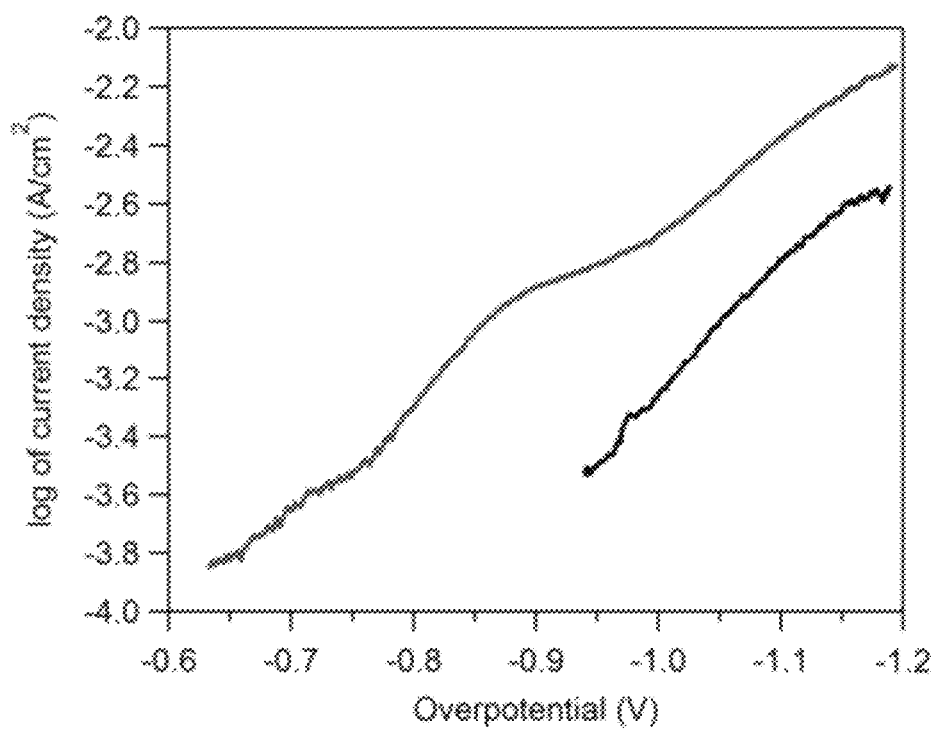
FIG. 18 illustrates Tafel plots of 3.7 µM 2 (red) and background (black) in 0.05 M phosphate buffer at pH 7 (scan rate: 5 mV/s).

Cyclic voltammetry experiments were performed on an aqueous solution of compound 2 maintained at pH 7 using phosphate buffer. A mercury pool electrode was employed in these measurements, owing to its low activity for water reduction and correspondingly large reductive window. For the buffered electrolyte alone, no catalytic current arises until the potential is scanned beyond −1.6 V vs. SHE (FIG. 2). Upon addition of 2, however, a peak at −1.00 V vs. SHE, corresponding to the Co(II)/Co(I) reduction, is followed by a sharp increase in current beginning at −1.20 V vs. SHE This rise in current, which coincides with the evolution of bubbles, can be attributed to the catalytic generation of $H_2$ from neutral water. Using a controlled growth mercury drop electrode as the working electrode owing to its smaller background current, we scanned the cyclic voltammogram of 2 to more negative potentials (FIG. 13). in addition to the first reduction peak at −1.00 V vs. SHE, which is partially proton coupled based on the pH dependence studies (FIG. 14), a second reduction peak (−1.21 V vs. SHE) appears at the rise of the catalytic current and is pH independent (FIGS. 13-14). Furthermore, it was found the catalytic current maximum of 2 is dependent on catalyst concentration (FIG. 15) but independent of scan rate (FIG. 17), indicating the catalyst is functioning in a diffusion controlled regime and is molecular in nature.

Figure 3:
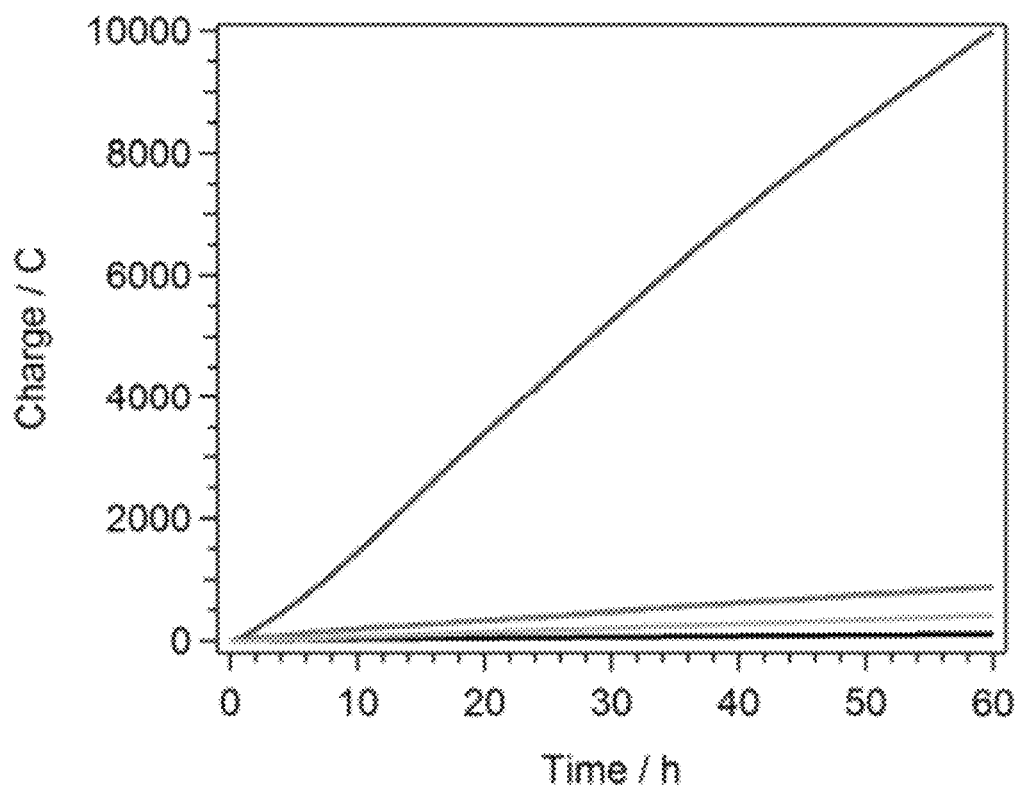
FIG. 3 is a plot of the extended controlled potential electrolysis of Co(II)-PY5Me$_2$ complex 4.7 µM 2 (red), 8.9 µM Zn(II)-PY5Me$_2$ complex 3 (orange), 6.2 µM PY5Me$_2$ (green), and blank control (black) in aqueous solution buffered to neutral pH (2.0 M phosphate, pH 7) showing charge build-up versus time with an applied potential of −1.30 V vs. SHE. Only the Co(II)-PY5Me$_2$ complex 2 is active for generating H$_2$ from water.

FIG. 3 the extended controlled potential electrolysis of Co(II)-$PY5Me_2$ complex 4.7 μM 2 (red), 8.9 μM Zn(II)-$PY5Me_2$ complex 3 (orange), 6.2 μM $PY5Me_2$ (green), and blank control (black) in aqueous solution buffered to neutral pH (2.0 M phosphate, pH 7) showing charge build-up versus time with an applied potential of −1.30 V vs. SHE. Only the Co(II)-PY5Me$_2$ complex 2 is active for generating H$_2$ from water.

A number of control experiments were carried out to verify that [(PY5Me$_2$)Co(H$_2$O)]$^{2+}$ is responsible for the catalysis. In particular, the free PY5Me$_2$ ligand, CoCl$_2$, and compound 3, featuring the analogous complex of the redox-inactive Zn(II) ion, were each measured under identical conditions. As shown in FIG. 2, the catalytic competency achieved with 2 is not matched by just PY5Me$_2$ or [Co(H$_2$O)$_6$]$^{2+}$, as might arise from dissociation of the ligand, nor can it be accomplished with the PY5Me$_2$ ligand bound to a redox-inactive metal. Thus, a combination of the redox-active cobalt ion and the ancillary ligand is essential for catalytic activity.

Figure 19:
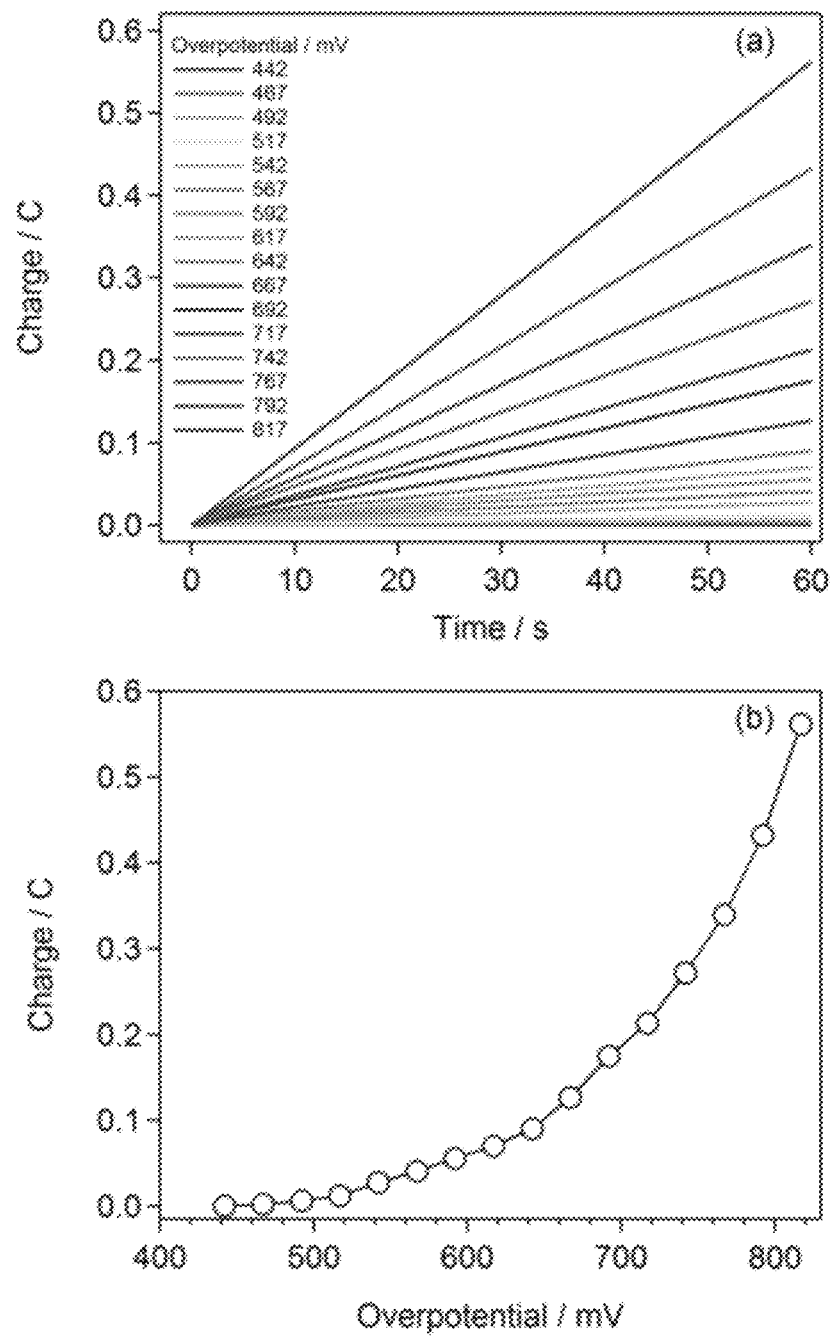
FIG. 19 illustrates (a) charge build-up versus time and (b) the accumulated charge at the end of 1 min for the controlled. potential electrolysis of a 38 µM solution of 2 in water buffered to neutral pH (1.0 M phosphate, pH 7) at various overpotentials. 0.12 C charge was used to fully reduce the cobalt catalyst in the bulk solution by one electron.

To assess the overpotential required for electrochemical production of H$_2$ from water in the presence of 2, controlled potential electrolysis (CPE) experiments were performed using a custom-made double-compartment cell (FIG. 19). Charge build-up at various applied potentials was monitored over the course of 1 min electrolyses performed on a 38 μM solution of 2 in water buffered at pH 7. As shown in FIG. 11, the total charge consumed is negligible for overpotentials below −0.52 V and increases approximately linearly with time at more negative applied potentials. Importantly, the onset of the catalytic current occurs at an overpotential of −0.66 V (−1.07 V vs. SHE), which is just slightly more negative than the Co(II)/Co(I) reduction potential.

Figure 20:
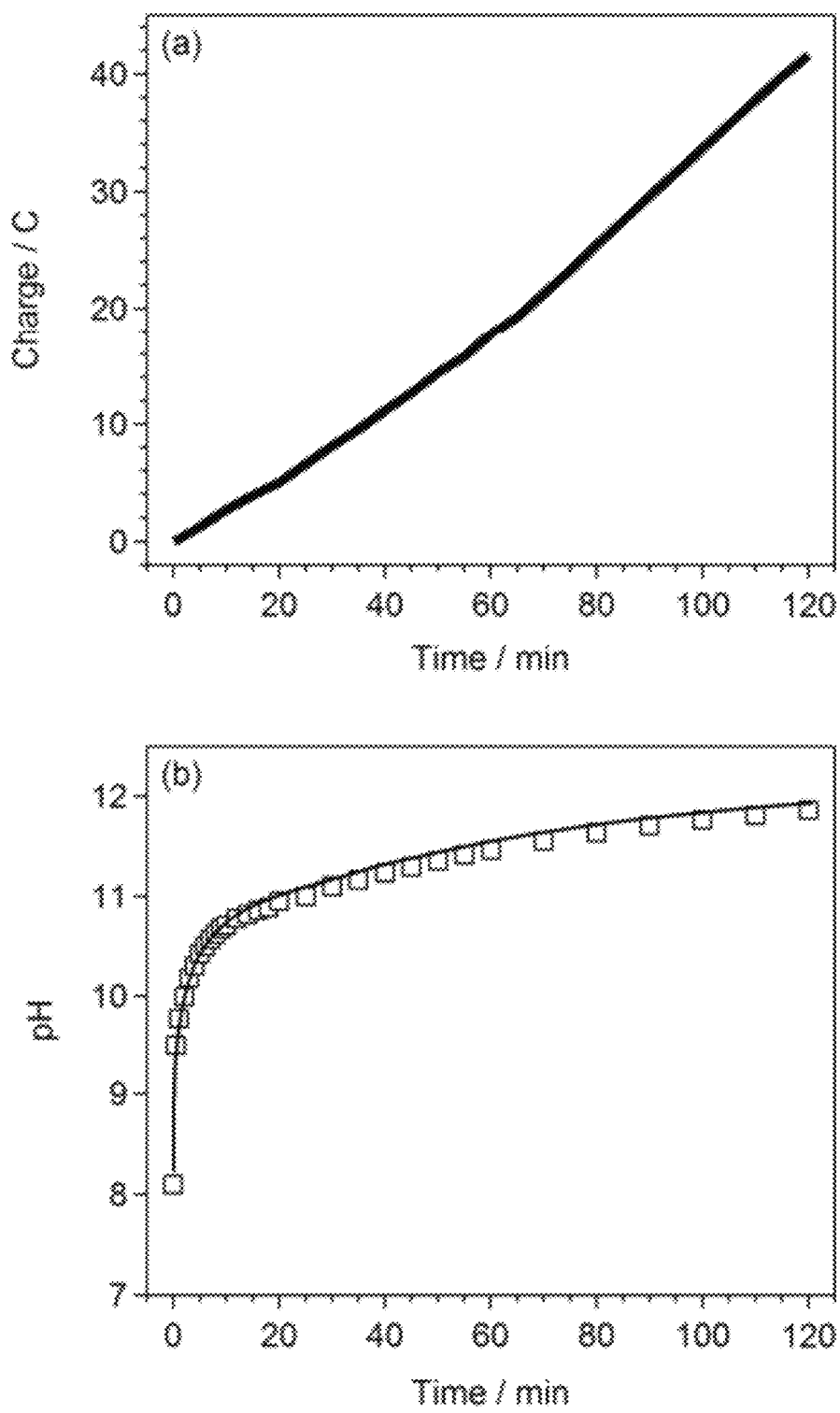
FIG. 20 illustrates (a) charge build-up over time during the electrolysis of 15.6 µM 2 in 1.0 M KCl at an applied potential of −1.4 V vs. SHE. (b) Measured (squares) and calculated (solid line) pH changes assuming a 100% Faradaic efficiency of 2 during the electrolysis.
Figure 21:
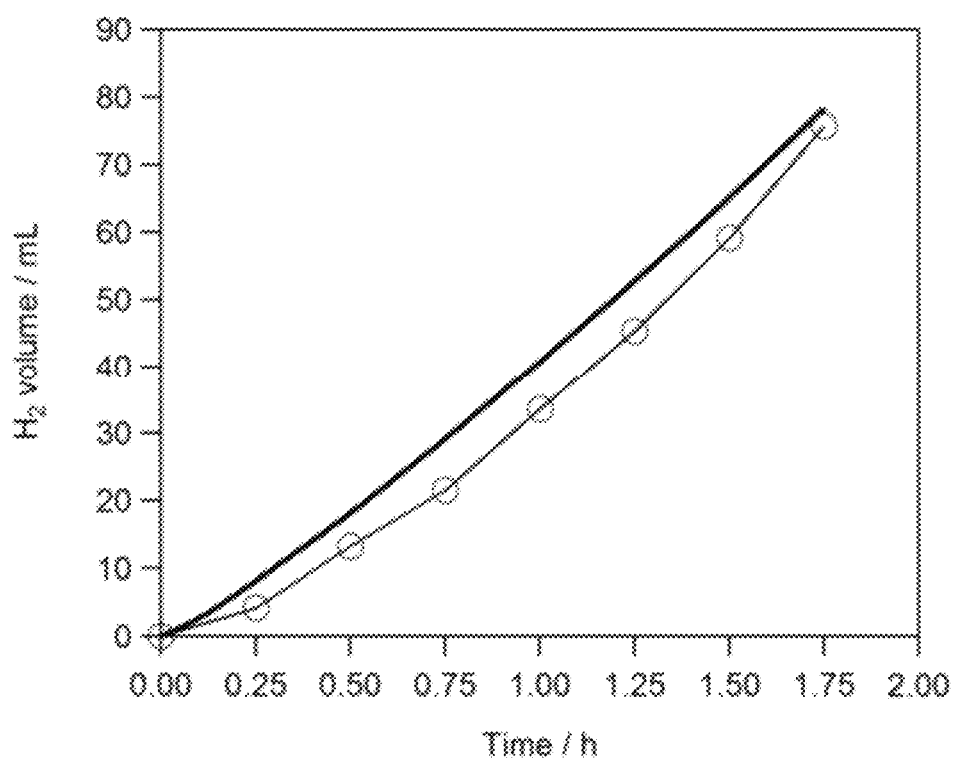
FIG. 21 illustrates generated hydrogen volume calculated from passed charge (black solid) and measured from gas chromatography (white circle) during the electrolysis of 3.2 µM 2 in 1.0 M phosphate buffer (pH 7) with an applied potential of −1.4 V vs. SHE.

To estimate the Faradaic efficiency for H$_2$ production by the catalyst, a two-hour CPE experiment was performed in a 1.0 M aqueous potassium chloride solution (FIG. 20). The evolution of H$_2$ during the experiment was confirmed by mass spectral analysis. For each H$_2$ molecule liberated, two OH$^-$ anions are left behind, resulting in an increase in the pH of the solutions and providing a simple means of quantifying the amount of H$_2$ produced. The observed rise in pH during the course of the CPE measurement closely matches that calculated based on the amount of charge consumed. The generated H$_2$ volume was also directly measured via gas chromatography and overlaps well with the amount calculated from consumed charge (FIG. 21). The data from both methods establish that catalyst 2 operates at close to 100% Faradaic efficiency, meaning that every electron goes toward H$_2$ production without generation of wasteful organic byproducts.

Figure 22:
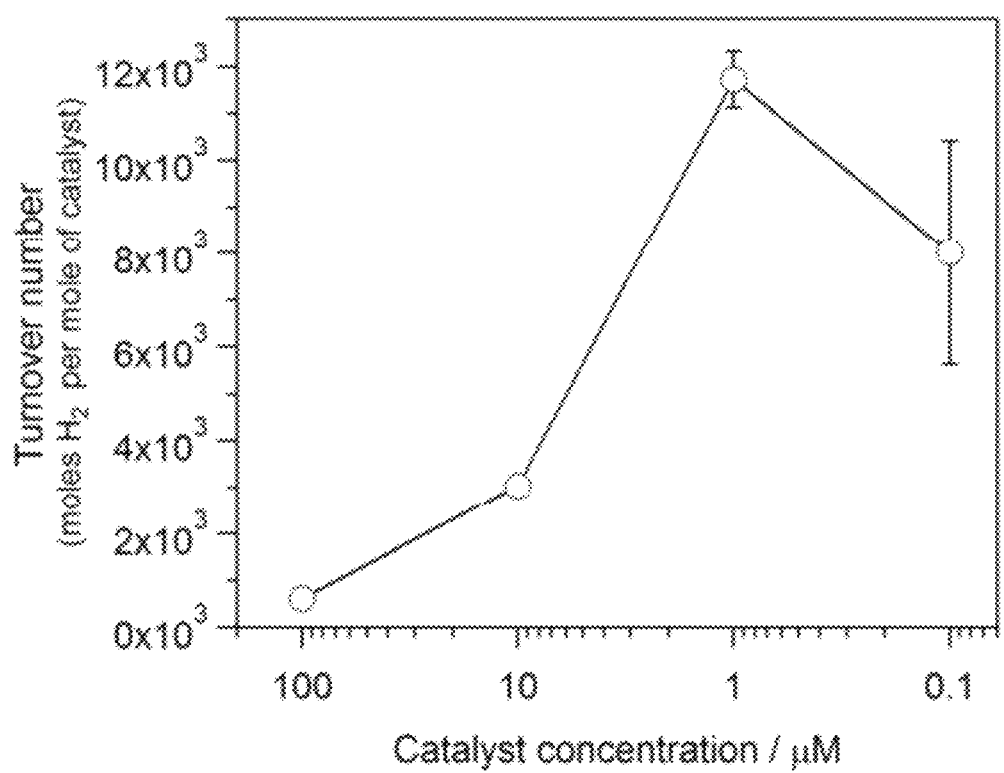
FIG. 22 illustrates calculated turnover number of H$_2$ evolution versus the bulk concentration of 2 during a 12 h electrolysis with an applied potential of −1.3 V vs, SHE in a 2.0 M phosphate buffer at pH 7.

The durability of catalyst 2 was assessed in an extended CPE experiment performed in water and maintained at pH 7 with 2.0 M phosphate buffer. To ensure a rapid turnover rate during the electrolysis, a potential of −1.30 V vs. SUE was employed for the measurement. As depicted in FIG. 3, the catalyst affords a robust and essentially linear charge build-up over time, with no substantial loss in activity over the course of 60 h, Significantly, control experiments employing either the free PY5Me$_2$ ligand or the analogous Zn(II) compound 3 show little or no activity under the same conditions. Based on the bulk concentration of 2 (4.7 μM) used in the experiment, a turnover number (TON) of $5.5 \times 10^4$ moles of H$_2$ per mole of catalyst is calculated. This value is significantly greater than has been reported for other molecular cobalt catalysts for electrochemical H$_2$ production in neutral water. It is important to note that the TON obtained for 2 is a conservative underestimate, since only the small fraction of catalyst molecules interacting with the electrode are contributing to H$_2$ production. Indeed, a series of 12-h CPE experiments indicated that the calculated TON and associated turnover frequency (TOP) depend upon the concentration of 2 used in the experiment, with the latter reaching a maximum value of 0.3 moles of H$_2$ per mole of catalyst per second (FIG. 22), In addition, the CPE experiment was terminated after 60 h only due to depletion of the buffer capacity at high concentrations of hydroxide ions, as we observe no degradation of the Co catalyst within this timeframe. Taken together, these data establish compound 2 as a robust and active catalyst for H$_2$ generation from neutral water.

Figure 4:
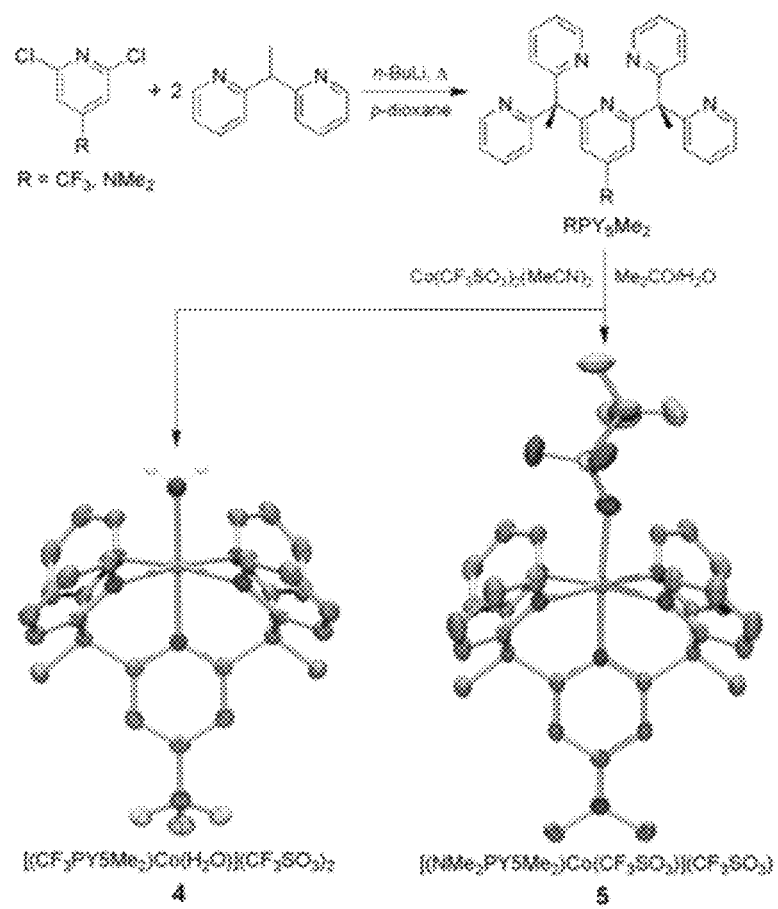
FIG. 4 illustrates the syntheses of the new pentapyridine ligands RPY5Me$_2$ (R=CF$_3$, NMe$_2$) and compounds 4 and 5, and the crystal structures of the resulting complexes $[(CF_3PY5Me_2)Co(H_2O)]^{2+}$ and $[(NMe_2PY5Me_2)Co(CF_3SO_3)]^+$, with thermal ellipsoids drawn at the 75% and 50% probability level, respectively. Selected interatomic distances (Å) and angles (deg) for 4 and 5, respectively: Co—N 2.124(2)-2.133(2), 2.065(4)-2.133(3); Co—O 2.050(3), 2.118(5); N—Co—N 81.06(8)-98.96(8), 81.34(10)-99.54(14), N—Co—O 92.7(1)-94.0(1), 87.2(6)-96.9(6).s a plot of extended electrolysis data for a 2 µM solution of $[(PY5Me_2)MoO](PF_6)_2$ in a 3 M pH7 phosphate buffer.

FIG. 4 the syntheses of the new pentapyridine ligands RPY5Me$_2$ (R=CF$_3$, NMe$_2$) and compounds 4 and 5, and the crystal structures of the resulting complexes [(CF$_3$PY5Me$_2$)Co(H$_2$O)]$^{2+}$ and [NMe$_2$PY5Me$_2$)Co(CF$_3$SO$_3$)]$^+$, with thermal ellipsoids drawn at the 75% and 50% probability level, respectively. Selected interatomic distances (Å) and angles (deg) for 4 and 5, respectively: Co—N 2.124(2)-2.133(2), 2.065(4)-2.133(3); Co—O 2.050(3), 2.118(5); N—Co—N 81.06(8)-98.96(8), 81.34(10)-99.54(14), N—Co—O 92.7(1)-94.0(1), 87.2(6)-96.9(6).

A key advantage of a well-defined molecular catalyst lies in the possibility of tuning its performance via synthetic chemistry. The parent [(PY5Me$_2$)Co(H$_2$O)]$^{2+}$ is indeed a highly robust and active catalyst based upon an earth-abundant metal, but it is still necessary to lower the overpotential at which it operates. As an initial test of the tunability of this system, two new derivatives of PY5Me$_2$ with substituents placed at the para position of the central pyridine ring were synthesized (FIG. 4): 4-trifluoromethyl-2,6-bis(1,1-di(pyridin-2-yl)ethyppyridine (CF$_3$PY5Me$_2$), featuring an electron-withdrawing CF$_3$ group, and 4-dimethylamino-2,6-bis(1,1-di(pyridin-2-ypethyl)pyridine (NMe$_2$PY5Me$_2$), featuring an electron-donating NMe$_2$ group. A metallation procedure directly analogous to that employed in the preparation of 2 afforded the compounds [CF$_3$PY5Me$_2$)Co(H$_2$O)](CF$_3$SO$_3$)$_2$ (4) and [NMe$_2$PY5Me$_2$)Co(CF$_3$SO$_3$)](CF$_3$SO$_3$) (5). Single-crystal X-ray analysis for the compounds revealed the structures of the octahedral [(RPY5Me$_2$)CoX]$^{2+}$(X=H$_2$O for 2 and 4, CF$_3$SO$_3^-$ for 5) complexes to be nearly congruent. It is anticipated that the bound CF$_3$SO$_3^-$ anion in 5 will be easily replaced by a H$_2$O molecule when 5 is dissolved in an aqueous solution, resulting in the formation of [NMe$_2$PY5Me$_2$)Co(H$_2$O)]$^{2+}$.

Figure 23:
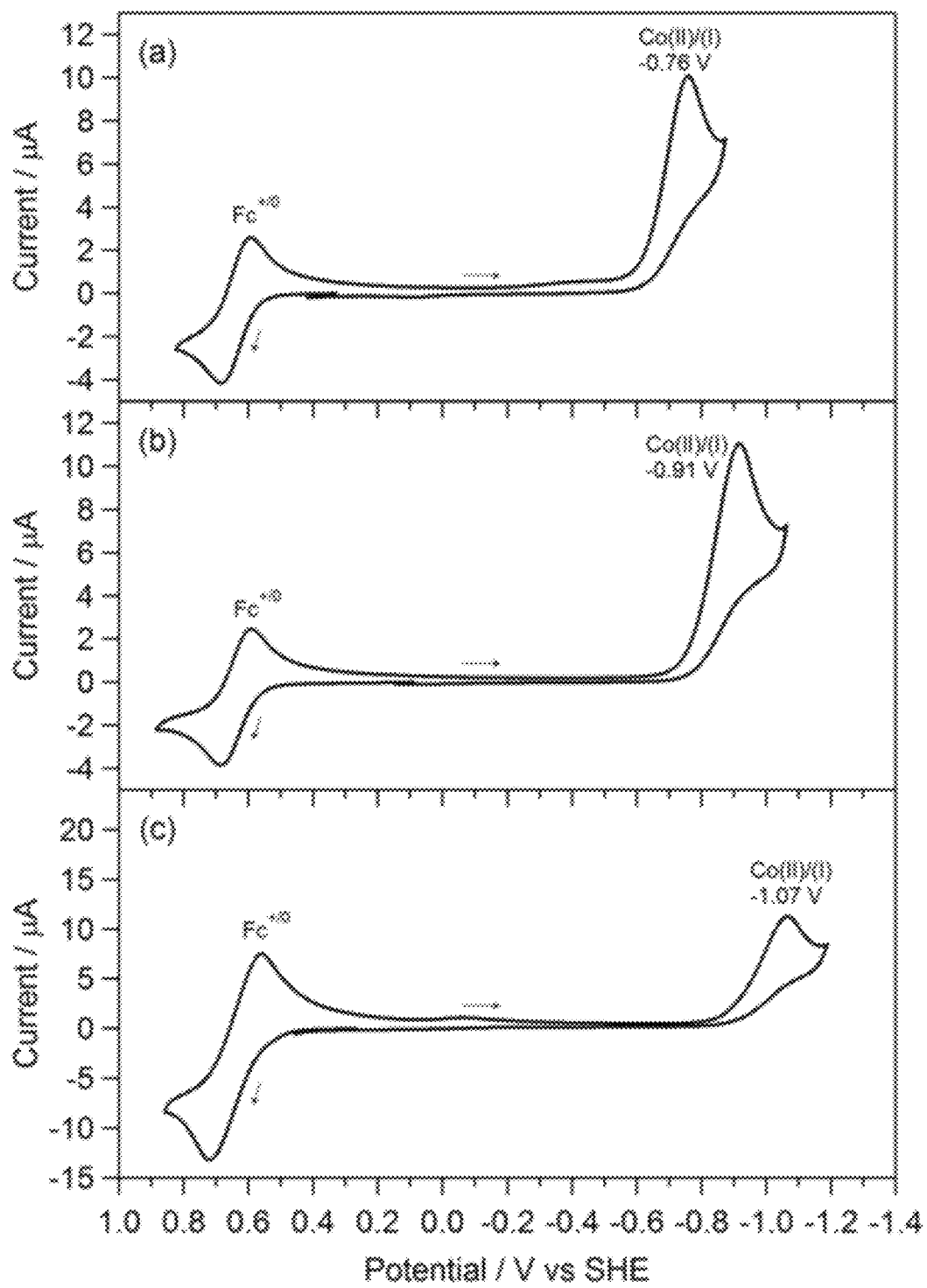
FIG. 23 illustrates cyclic voltammograms of complexes 4 (a), 2 (b), and 5 (c) in CH$_2$Cl$_2$ showing their first reduction peaks assigned to Co(II)/Co(I) reduction processes. The ferrocene peaks ($E_{Fc}^{+/0}$=0.64 V vs. SHE) are included as the external reference standard (scan rate: 100 mV/s).
Figure 24:
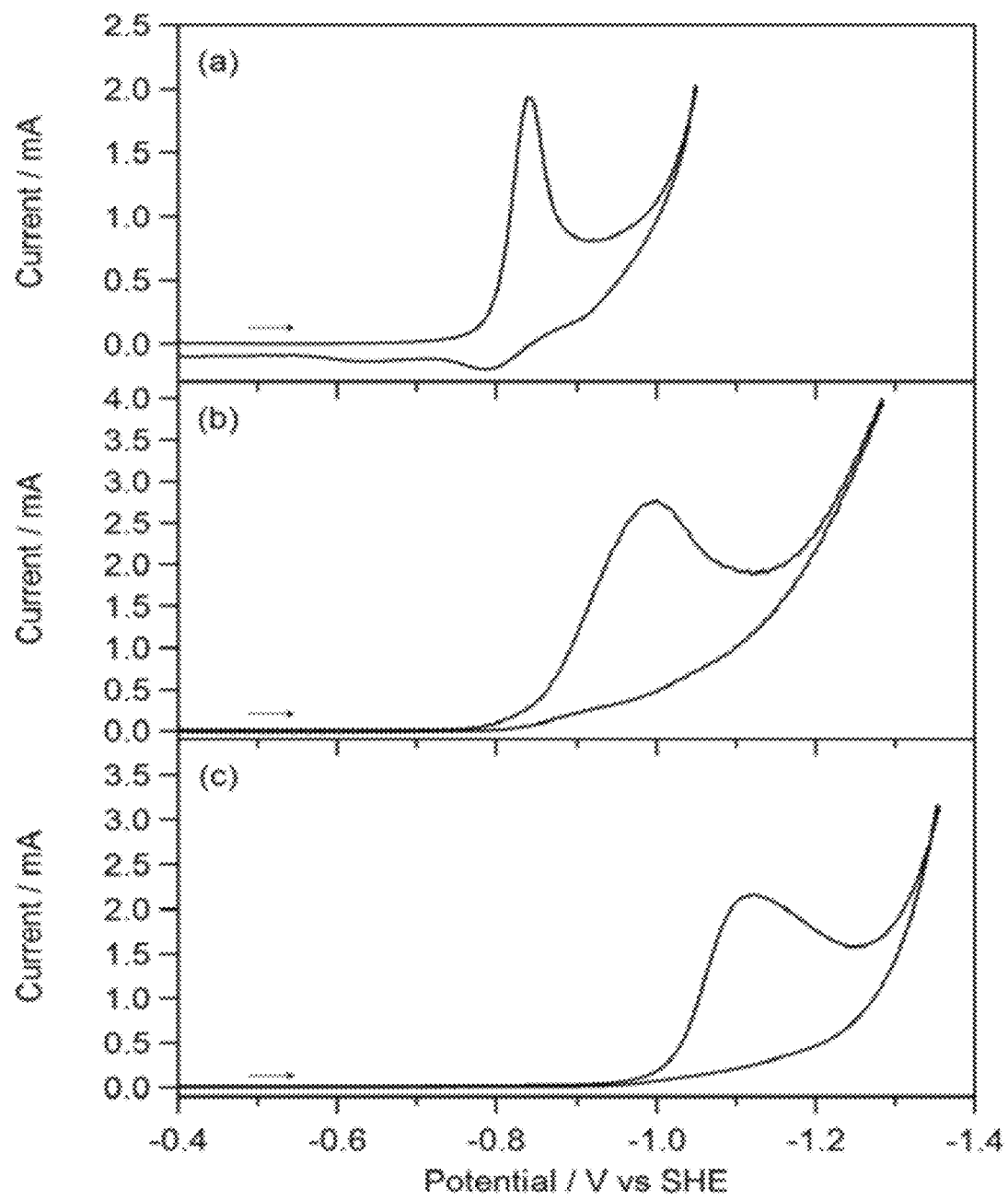
FIG. 24 illustrates cyclic voltammograms of 8.9 µM 4 (a), 6.1 µM 2 (b), and 7.2 µM 5 (c) in 2.0 M phosphate buffer at pH 7 (scan rate: 100 mV/s).

Electrochemical measurements show that indeed the Co—PY5Me$_2$ catalyst is highly tunable, with even these substitutions on a single pyridine ring leading to significant shifts in the reduction potentials. The cyclic voltammograms of compounds 2, 4, and 5 in CH$_2$Cl$_2$ are compared in FIG. 23. As expected, the primary Co(II)/Co(I) reduction potentials track systematically with the electronic nature of the substituent. Thus, the complex with the electron-withdrawing CF$_3$ group exhibits the most positive reduction potential (−0.76 vs. SHE) compared to the parent complex (−0.91 vs. SHE), while the congener with the electron-donating NMe$_2$ group is shifted to more negative potentials (−1.07 V vs. SHE).

Figure 5:
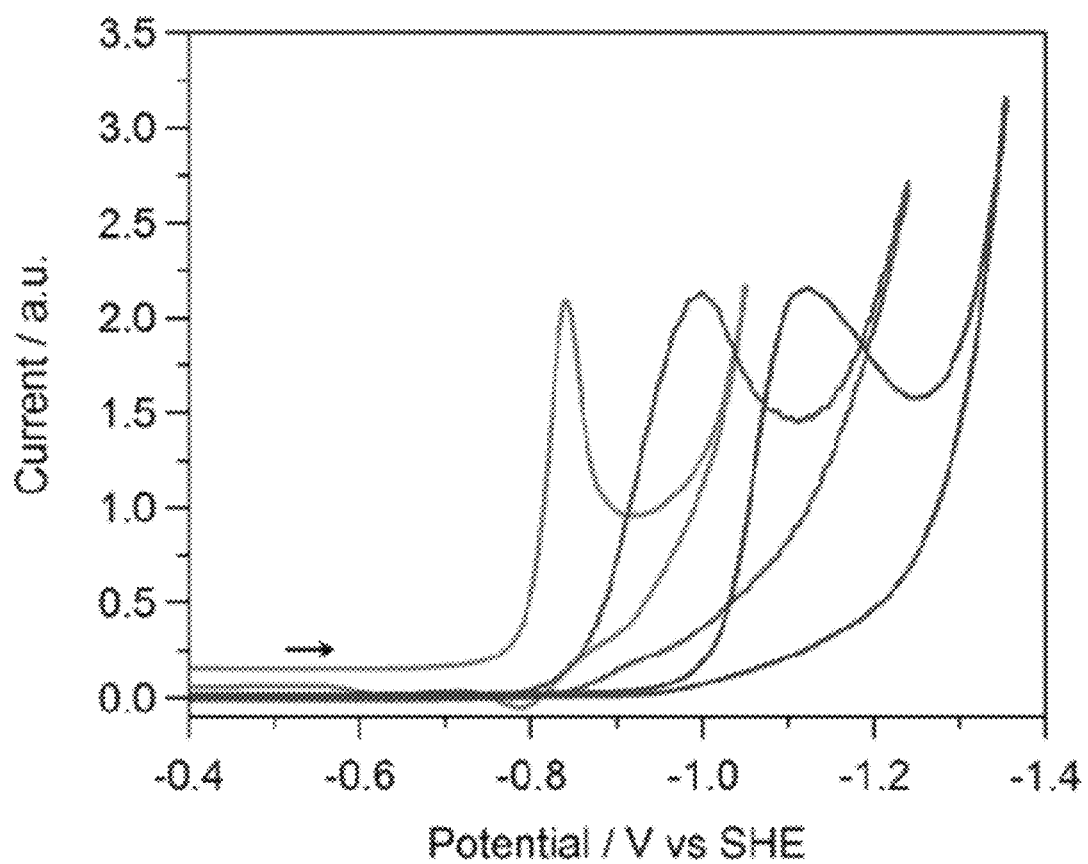
FIG. 5 is a plot of normalized cyclic voltammograms of Co—PY5Me$_2$ derivatives, showing the parent 2 (red), CF$_3$-substituted 4 (green), and NMe$_2$-substituted 5 (blue) versions in aqueous solution maintained at pH 7 with a 1.0 M phosphate buffer.

FIG. 5 which illustrates normalized cyclic voltammograms of Co—PY5Me$_2$ derivatives, showing the parent 2 (red), CF$_3$-substituted 4 (green), and NMe$_2$-substituted 5 (blue) versions in aqueous solution maintained at pH 7 with a 1.0 M phosphate buffer.

As shown in FIG. 5, similar shifts are apparent for experiments conducted in neutral aqueous media, with the Co(II)/Co(I) reduction peaks occurring at −0.84, −1.00, and −1.12 V vs. SHE for 4, 2 and 5, respectively. Most importantly, the subsequent sharp rise in current shifts in the same manner, indicating that the substitutions do in fact adjust the potential at which catalysis arises. The foregoing results demonstrate [(PY5Me$_2$)Co(H$_2$O)]$^{2+}$ to be an active and long-lived catalyst for the generation of hydrogen from neutral water. Significantly, peripheral substitutions on the PY5Me$_2$ ligand are seen to shift the potential required for catalysis in a logical manner, opening the way to the design of analogs that operate at much lower overpotentials. Future work will focus on the synthesis of variants of the complex bearing additional electron-withdrawing substituents, and on establishing the mechanism by which the new catalysts are functioning. Light-driven hydrogen generation by these catalysts in the presence of photosensitizers is also under investigation.

Materials 1,1-Bis(2-pyridyl)ethane, 2,6-bis[2-ppyridyl)ethyl]pyridine ($PY5Me_2$), and 4-dimethylamino-2,6-difluoropyridine were synthesized as previously reported. 2,6-Dichloro-4-(trifluoromethyl)pyridine was purchased from Oakwood Products and used as received. Electronic grade Hg (99.9998%), glassy carbon rods (type 1), and platinum gauze were purchased from Alfa Aesar for the electrochemical studies. Acetonitrile and dichloromethane were dried over activated 4 Å molecular sieves, passed through a column of activated alumina, and stored over 3 Å molecular sieves under a nitrogen atmosphere, p-Dioxane was distilled. over sodium under nitrogen atmosphere. Water was deionized with the Millipore UF Plus system. All other chemical regents were purchased from commercial vendors and used without further purification, Unless noted otherwise, all manipulations were carried out at room temperature under a nitrogen atmosphere in a VAC glovebox or using high-vacuum Schlenk tine techniques.

Syntheses

4-Trifluoromethyl-2,6-bis(1,1-di(pyridin-2-yl)ethyl)pyridine ($CF_3PY5Me_2$). 10 g of 1,1-bis(2-pyridyl)ethane was stirred in 160 mL of p-dioxane at −78° C. (dry ice/acetone bath), followed by slow addition of 40 mL "BuLi (1.6 M in hexanes). Stirring was continued for 15 min, and then 4.78 g 2,6-dichloro-4-(trifluoromethyppyridine in 25 mL of p-dioxane was slowly added via cannula. The solution was allowed to gradually warm to room temperature and followed by refluxing of 48 h. The mixture was then quenched with 80 mL $H_2O$ and the organic and aqueous layers were separated. The aqueous layer was extracted with dichloromethane (3×50 mL) and the organic portions were combined and dried over $Na_2SO_4$. After filtration using a coarse sintered glass frit, the solvent was removed under reduced pressure to obtain a dark red oil. The residue was diluted with ~10 mL of dichloromethane and layered with ~30 mL of diethylether prior to cooling to −20° C. The light yellow product was separated after one day and collected by filtration and washed with 50 mL of diethylether. Yield: 7.72 g (68%). $^1$H NMR ($CDCl_3$, 400 MHz): δ =8.51 (dd, J=4.84, 0.96 Hz, 4H), 7.47 (t, J=7.30, 7.30 Hz, 4H), 7.34-7.27 (m, 2H), 7.10 (dd, J=6.65, 5.38 Hz, 4H), 6.88 (d, J=7.77 Hz, 4H), 2.22 (s, 6H). Anal. Calcd. for $C_{30}H_{24}F_3N_5$: C, 70.44%; H, 4.73%; N, 13.69%. Found: C, 70.06%; H, 5.03%; N, 13.47%. LCMS (M$^+$) m/z calcd for $[CF_3PY5Me_2+H]^+$, 512.2062, found 512.2.

4-Dimethylamino-2,6-bis(1,1-di(pyridin-2-yl)ethyl)pyridine ($NMe_2PY5Me_2$). $NMe_2PY5Me_2$ was synthesized in a similar manner as that of $CF_3PY5Me_2$, using 1,1-bis(2-pyridyl)ethane and 4-dimethylamino-2,6-difluoropyridine as the precursors, and purified on a silica column eluted with $CH_2Cl_2$:MeOH:triethytamine (20:1:0.1). Yield: 61%. $^1$H NMR ($CDCl_3$, 400 MHz): □=8.44 (dd, J=4.81, 0.98 Hz, 4H), 7.28 (dt, J=7.86, 7.80, 1.89 Hz, 4H), 6.95 (ddd, J=7.41, 4.85, 0.98 Hz, 4H), 6.76 (d, J=8.05 Hz, 4H), 6.31 (s, 2H), 2.80 (s, 6H), 2.13 (s, 6H). Anal. Calcd. for $C_{31}H_{30}N_6$: C, 76.52%; H, 6.21%; N, 17.27%. Found: C, 76.22%; H, 6.46%; N, 17.15%. LMS (M$^+$) m/z calcd for $[NMe_2PY5Me_2+H]^+$, 487.2610, found, 487.3.

$[(PY5Me_2)Co(NCCH_3)](CF_3SO_3)_2$ (1). 1 eq of $Co(CF_3SO_3)_2(CH_3CN)_2$ (175 mg) was added to a 5 mL aceto- nitrile suspension of $PY5Me_2$ (177 mg), The mixture was stirred under nitrogen atmosphere at room temperature for 5 h. The orange solution was then concentrated to ~1 mL under vacuum and diethyl ether vapor diffusion into this solution generated rod-shape light brown crystals suitable for X-ray crystallography. Yield: 312 mg (93%). Anal. Calcd. for $C_{33}H_{28}CoF_6N_6O_6S_2.H_2O$: C, 46.10%; H, 3.52%; N, 9.78%. Found: C, 46.19%; H, 3.65%; N, 9.91%, HRESIMS (M$^+$) m/z calcd for $C_{30}H_{25}CoF_3N_5O_3S$ 651.0962, found 651.0947.

$[(PY5Me_2)Co(OH_2)](CF_3SO_3)_2$ (2). $Co(CF_3SO_3)_2(CH_3CN)_2$ (193 mg) and $PY5Me_2$ (195 mg) were added to a 10 mL mixture of acetone/water (9/1). The mixture was stirred under nitrogen atmosphere at room temperature for 5 h, then concentrated to ~1 mL under vacuum. Light brown crystals suitable for X-ray crystallography were obtained via diethyl ether vapor diffusion into this solution over a period of two days, Yield: 325 mg (90%). Anal. Calcd. for $C_{31}H_{27}CoF_6N_5O_7S_2$: C, 45.48%; H, 3.32%; N, 8.55%. Found: C, 45.51%; H, 3.26%; N, 8.50%. HRESIMS (M$^{30}$) m/z calcd for $C_{30}H_{25}CoF_3N_5O_3S$ 651.0957, found 651.0961. Magnetic susceptibility (d$^6$-Acetone): $\mu_{eff}$=4.26 $\mu_{BM}$.

$[(PY5Me_2)Zn(OH_2)](CF_3SO_3)_2$ (3). $ZnCl_2$ (134 mg) and $PY5Me_2$ (444 mg) were added to a 8 mL mixture of acetone/water (3/1). The mixture was stirred under nitrogen atmosphere at room temperature over night. White solids were obtained after solvent removal. Yield: 636 mg (77%). White crystals suitable for X-ray crystallography were obtained via diethyl ether vapor diffusion into a. concentrated acetone solution of 3 over night. Anal. Calcd. for $C_{32}H_{26}F_9N_5O_7S_2Zn$: C, 45.13%; H, 3.30%; N, 8.49%. Found: C, 45.25%; H, 3.44%; N, 8.43%. HRESIMS (M$^+$) m/z calcd for $C_{30}H_{25}F_3N_5O_3SZn$ 656.0922, found 656.0920.

$[(CF_3PY5Me_2)Co(OH_2)](CF_3SO_3)_2$ (4). $Co(CF_3SO_3)_2(CH_3CN)_2$ (193 mg) and $CF_3PY5Me_2$ (226 mg) were added to a 20 mL mixture of acetone/water (9/1). The mixture was stirred under nitrogen atmosphere at room temperature over night. Yellow solids were obtained after solvent removal. Yield: 358 mg (92%). Light yellow crystals suitable for X-ray crystallography were obtained via diethyl ether vapor diffusion into a concentrated acetone solution of 4 over a period of two days. Anal. Calcd. for $C_{33}H_{32}CoF_6N_6O_7S_2.H_2O$: C, 45.05%; H, 3.90%; N, 9.55%. Found: C, 45.60%; H, 4.12%; N, 9.10%. HRESIMS (M$^+$) m/z calcd for $C_{31}H_{24}CoF_6N_5O_3S$ 719.0836, found 719.0823.

$[(NMe_2PY5Me_2)Co(CF_3SO_3)]CF_3SO_3$ (5). $Co(CF_3SO_3)_2(CH_3CN)_2$ (220 mg) and $NMe_2PY5Me_2$ (245 mg) were added to a 20 mL mixture of acetone/water (9/1). The mixture was stirred under nitrogen atmosphere at room temperature over night. Yellow solids were obtained after solvent removal. Yield: 343 mg (81%). Yellow crystals suitable for X-ray crystallography were obtained via diethyl ether vapor diffusion into a deaerated acetone solution of 5 under $N_2$ overnight. Anal. Calcd. for $C_{30}H_{30}CoF_6N_6O_6S_2$: C, 46.98%; H, 3.58%; N, 9.96%. Found: C, 47.15%; H, 3.95%; N, 9.70. HRESIMS (M$^+$) m/z calcd for $C_{32}H_{30}CoF_3N_6O_3S$ 694.1384, found 694.1385.

Physical Methods

Carbon, hydrogen, and nitrogen analyses were obtained from the Microanalytical Laboratory of the University of California, Berkeley. Mass spectra were determined at the University of California, Berkeley Mass Spectrometry Facility. Magnetic susceptibility measurements were made using Evans' method: an NMR tube containing the paramagnetic compound with one drop of $CH_2Cl_2$ in deuterium acetone (or acetonitrile) was fitted with an insert containing only one drop of $CH_2Cl_2$ in the deuterium solvent. The paramagnetic shift of the $CH_2Cl_2$ signal was used to calculate the room temperature solution magnetic moment. Cyclic voltammetry experiments were carried out using BASI's Epsilon potentiostat and C-3 cell stand. A glassy carbon working electrode and two platinum wires were used for cyclic voltammetry experiments in $CH_3CN$ and $CH_2Cl_2$ with 0.1 M $Bu_4NPF_6$ in glovebox. Ferrocene ($E_{Fc}^{+/0}$=0.64 V vs. SHE) was added during each experiment as an internal reference.

For electrochemical studies conducted in aqueous media, a mercury pool with a surface area of 19.6 $cm^2$ was used as the working electrode, which was stirred constantly during controlled potential electrolysis experiments. Electrical contact of the mercury pool was achieved through a platinum wire immersed below the surface of the mercury. A 20.5 $cm^2$ platinum gauze (52 mesh, woven from 0.1-mm-diameter wire) was used as the auxiliary electrode and was separated from the solution of the working electrode by a medium-porosity sintered-glass frit, The reference electrode was a commercially available aqueous Ag/AgCl electrode, and the potentials were reported with respect to SHE by adding 0.195 V to the experimentally measured values. The working and auxiliary compartments both contained 200 mL electrolyte solutions, which were thoroughly deaerated via bubbling water-saturated nitrogen 15 min prior to and during the experiments. iR (current times internal resistance) compensation was used in all experiments to account for the voltage drop between the reference and working electrodes using the software supplied with the BASI Epsilon potentiostat. The cyclic voltammetry studies in FIGS. 13-18 were conducted using a controlled-growth mercury electrode (Bioanalytical systems) as the working electrode with a drop size of 0.0116 $cm^2$ and a glassy carbon rod auxiliary electrode and an aqueous Ag/AgCl reference electrode.

Determination of Faradaic Efficiency

Figure 12:
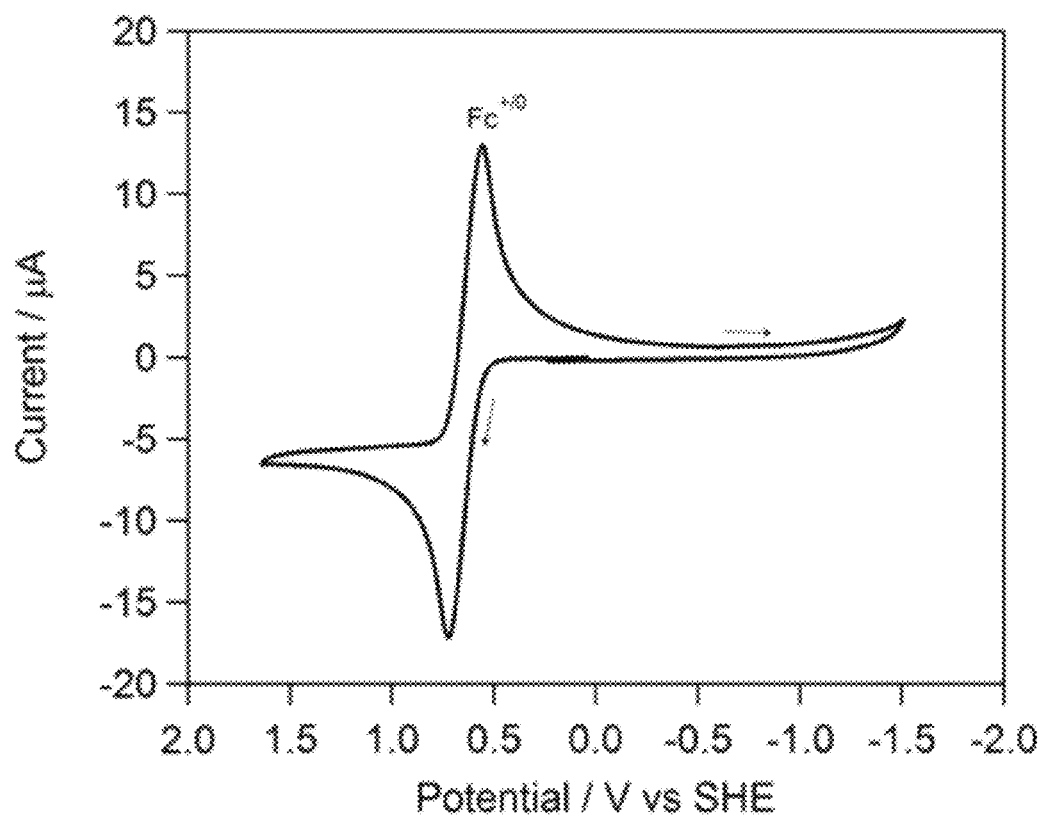
FIG. 12 illustrates cyclic voltammogram of 3 in CH$_2$Cl$_2$ and the ferrocene peak ($E_{Fc}^{+/0}$=0.64 V vs. SHE) included as the reference (scan rate: 100 mV/s).

Controlled potential electrolyses were conducted for 15.6 μM solutions of 2 in a 200 mL 1 M KCl solution at an applied potential of –1.4 V vs. SHE for 2 hours, The charge build-up versus time was plotted in FIG. 12, The pH change of the solution during the electrolysis was recorded with a pH meter, and plotted against time in FIG. 20. Assuming 100% Faradaic efficiency, the theoretical pH change over time can be calculated by the equation of $$pH = 14 + \lg \frac{\sum It}{FV},$$

where I=current (A), t=time (s), F=Faraday constant (96485 C/mol), V=solution volume (0.2 L). The theoretical pH change versus time was also included in FIG. 20.

FIG. 21 illustrates the generated hydrogen volume during electrolysis of 3.2 μM 2 in 1.0 M phosphate buffer (pH 7) based on gas chromatography (Varian Micro-GC with a Molecular Sieve 5 Å column, 40 m) measurement and a calibration curve, where 5 mL methane was injected as an internal standard. The theoretical (assuming 100% Faradic efficiency) hydrogen volume based on the amount of consumed charge during the course of electrolysis was included in FIG. 21 as well.

Crystallographic Structure Determinations

The X-ray crystallographic data collections were carried out on a Bruker three-circle diffractometer mounted with an SMART 1000 detector using monochromated Mo Kα radiation (0.71073 Å) outfitted with a low-temperature, nitrogen-stream aperture (1 and 3-5) or on a Balker kappa geometry goniostat with a micro focus rotating anode source (MicroSTAR) of Cu Kα radiation (1.54178 Å), an APEXII CCD detector, and equipped with an Oxford Cryostream 700 (2). The structures were solved using either direct methods or the Patterson method in conjunction with standard difference Fourier techniques and refined by full-matrix least-squares procedures.4 A semi-empirical absorption correction (SAD-ABS) was applied to the diffraction data for all structures. All non-hydrogen atoms were refined anisotropically, and hydrogen atoms were treated as idealized contributions and refined isotropically, The hydrogen atoms for the water ligand in 2-4 were located in the difference map and refined semi-freely. A summary of crystallographic data for 1-5 is given in Table 1. All software used for diffraction data processing and crystal-structure solution and refinement are contained in the APEX2 program suite (Bruker AXS, Madison, Wis.).

TABLE 1

Crystallographic data for complexes 1-5.

|  | 1[a] | 2[b] | 3[a] | 4[a] | 5[a] |
|---|---|---|---|---|---|
| Formula | $C_{37}H_{34}CoF_6$—$N_8O_6S_2$ | $C_{31}H_{27}CoF_6$—$N_5O_7S_2$ | $C_{31}H_{27}F_6N_5$—$O_7S_2Zn$ | $C_{35}H_{36}CoF_9$—$N_5O_{10}S_2$ | $C_{41.25}H_{49}CoF_6$—$N_6O_{9.5}S_2$ |
| Formula weight | 923.77 | 818.63 | 825.07 | 980.74 | 1017.91 |
| T, K | 133 | 230 | 100 | 100 | 100 |
| Space group | P21/n | P-1 | P-1 | Pbcm | C2/m |
| Z | 4 | 2 | 2 | 4 | 4 |
| a, Å | 12.5624 (12) | 12.5749 (2) | 12.5328 (5) | 10.4204 (4) | 21.8445 (2) |
| b, Å | 15.9060 (15) | 12.5919 (2) | 12.6860 (5) | 22.6721 (8) | 15.8758 (1) |
| c, Å | 20.2570 (2) | 12.9974 (2) | 14.0939 (6) | 16.3644 (6) | 13.9791 (1) |
| α, (°) | 90.000 | 113.192 (1) | 90.454 (2) | 90.000 | 90.000 (0) |
| β, (°) | 91.067 (2) | 91.686 (1) | 116.072 (2) | 90.000 | 95.097 (1) |
| γ, (°) | 90.000 | 116.337 (1) | 119.587 (2) | 90.000 | 90.000 (0) |
| V, Å$^3$ | 4047.0 (7) | 1642.48 | 1676.19 (12) | 3858.5 (2) | 4828.8 (6) |
| $R_1$ (w$R_2$), %[c] | 5.91 (16.76) | 3.04 (8.19) | 3.12 (8.40) | 2.62 (6.67) | 6.11 (18.87) |

[a] Obtained with graphite-monochromated Mo Kα (λ = 0.71073) radiation.
[b] Obtained with HELIOS multilayer mirror monochromated Cu Kα (λ = 1.54178) radiation.
[c] $R_1 = \Sigma ||F_o| - |F_c||/\Sigma |F_o|$, w$R_2 = \{\Sigma[w(F_c^2 - F_o^2)^2]/\Sigma[w(F_o^2)^2]\}^{1/2}$

We claim:
1. An organo metal complex of the following formula:

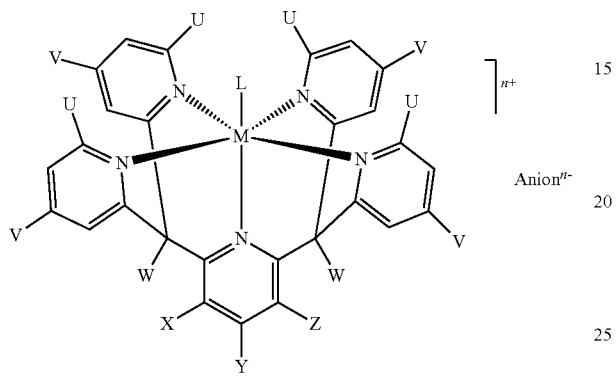

M=Co

U, V, W, X, Y, and Z are H, R, a halide, $CF_3$, $SiR_3$, where R can be an alkyl or aryl group L can be $H_2O$, $OH^-$, halide, alcohol, ether, thioether, amine, phosphine, nitrile, thiol, alkoxide, cyanide, isocyanide, azide, thiocyanate, aryl or alkyl sulfonate, phosphate, nitrate, sulfate n=0, 1, 2, or 3

Anions can be selected from chloride, phosphate, trifluoromethanesulfonate, and hexafluorophosphate.

* * * * *